US012597490B2

(12) United States Patent
Koller et al.

(10) Patent No.: US 12,597,490 B2
(45) Date of Patent: *Apr. 7, 2026

(54) METHODS AND SYSTEMS FOR MODELING PHASING EFFECTS IN SEQUENCING USING TERMINATION CHEMISTRY

(71) Applicant: LIFE TECHNOLOGIES CORPORATION, Carlsbad, CA (US)

(72) Inventors: Christian Koller, Groebenzell (DE); Marcin Sikora, Burlingame, CA (US); Peter Vander Horn, Encinitas, CA (US)

(73) Assignee: Life Technologies Corporation, Carlsbad, CA (US)

( * ) Notice: Subject to any disclaimer, the term of this patent is extended or adjusted under 35 U.S.C. 154(b) by 176 days.

This patent is subject to a terminal disclaimer.

(21) Appl. No.: 18/191,477

(22) Filed: Mar. 28, 2023

(65) Prior Publication Data

US 2023/0307095 A1 Sep. 28, 2023

Related U.S. Application Data

(63) Continuation of application No. 16/550,374, filed on Aug. 26, 2019, now Pat. No. 11,636,922, which is a continuation of application No. 14/506,520, filed on Oct. 3, 2014, now Pat. No. 10,410,739.

(60) Provisional application No. 61/886,878, filed on Oct. 4, 2013.

(51) Int. Cl.
| | |
|---|---|
| *G16B 40/10* | (2019.01) |
| *G16B 5/00* | (2019.01) |
| *G16B 20/00* | (2019.01) |
| *G16B 25/00* | (2019.01) |
| *G16B 30/00* | (2019.01) |
| *C12Q 1/6869* | (2018.01) |

(52) U.S. Cl.
CPC ............... *G16B 40/10* (2019.02); *G16B 5/00* (2019.02); *G16B 20/00* (2019.02); *G16B 25/00* (2019.02); *G16B 30/00* (2019.02); *C12Q 1/6869* (2013.01)

(58) Field of Classification Search
CPC .......... G16B 40/10; G16B 5/00; G16B 20/00; G16B 25/00; G16B 30/00; G16B 20/20; C12Q 1/6869
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 5,210,015 | A | 5/1993 | Gelfand et al. |
| 5,399,491 | A | 3/1995 | Kacian et al. |
| 5,587,128 | A | 12/1996 | Wilding et al. |
| 5,750,341 | A | 5/1998 | Macevicz |
| 5,854,033 | A | 12/1998 | Lizardi |
| 6,033,546 | A | 3/2000 | Ramsey |
| 6,054,034 | A | 4/2000 | Soane et al. |
| 6,174,670 | B1 | 1/2001 | Wittwer et al. |
| 6,210,891 | B1 | 4/2001 | Nyren et al. |
| 6,258,568 | B1 | 7/2001 | Nyren |
| 6,274,320 | B1 | 8/2001 | Rothberg et al. |
| 6,399,952 | B1 | 6/2002 | Maher et al. |
| 6,404,907 | B1 | 6/2002 | Gilchrist et al. |
| 6,613,525 | B2 | 9/2003 | Nelson et al. |
| 6,780,591 | B2 | 8/2004 | Williams et al. |
| 6,828,100 | B1 | 12/2004 | Ronaghi |
| 6,833,246 | B2 | 12/2004 | Balasubramanian |
| 6,911,327 | B2 | 6/2005 | McMillan et al. |
| 6,960,437 | B2 | 11/2005 | Enzelberger et al. |
| 7,037,687 | B2 | 5/2006 | Williams et al. |
| 7,049,645 | B2 | 5/2006 | Sawada et al. |
| 7,057,026 | B2 | 6/2006 | Barnes et al. |
| 7,133,782 | B2 | 11/2006 | Odedra |
| 7,211,390 | B2 | 5/2007 | Rothberg et al. |

(Continued)

FOREIGN PATENT DOCUMENTS

| | | |
|---|---|---|
| CN | 101389956 | 3/2009 |
| CN | 101627129 | 1/2010 |

(Continued)

OTHER PUBLICATIONS

Ahmadian et al., "Pyrosequencing: History, biochemistry and future," *Clinica Chimica Acta*, 363:83-94 (2006).
Anderson et al., "A System for Multiplexed Direct Electrical Detection of DNA Synthesis," *Sensors and Actuators B: Chemical*, 129(1):79-86 (2008).
Balzer et al., "Characteristics of 454 pyrosequencing data-enabling realistic simulation with flowsim," *Bioinformatics*, 26:1420-1425 (2010).
Barbaro et al., "Fully electronic DNA hybridization detection by a standard CMOS biochip," *Sensors and Actuators B: Chemical*, 118:41-46 (2006).

(Continued)

*Primary Examiner* — Soren Harward
*Assistant Examiner* — Dawn Bickham
(74) *Attorney, Agent, or Firm* — Jones Burke, PLLC

(57) ABSTRACT

A method for nucleic acid sequencing includes receiving nucleic acid sequencing data from a sequencing instrument that receives and processes a sample nucleic acid in a sequencing-by-synthesis process. The method also includes generating a set of candidate sequences of bases for the observed or measured nucleic acid sequencing data by determining a predicted signal for candidate sequences using a simulation framework. The simulation framework incorporates an estimated carry forward rate (CFR), an estimated incomplete extension rate (IER), an estimated droop rate (DR), an estimated reactivated molecules rate (RMR), and an estimated termination failure rate (TFR), the RMR being greater than or equal to zero and the TFR being lesser than one. The method also includes identifying, from the set of candidate sequences of bases, a candidate sequence as corresponding to the sequence for the sample nucleic acid.

15 Claims, 17 Drawing Sheets

(56) References Cited

U.S. PATENT DOCUMENTS

| | | | |
|---|---|---|---|
| 7,244,559 B2 | 7/2007 | Rothberg et al. | |
| 7,264,929 B2 | 9/2007 | Rothberg et al. | |
| 7,323,305 B2 | 1/2008 | Leamon et al. | |
| 7,335,762 B2 | 2/2008 | Rothberg et al. | |
| 7,348,181 B2 | 3/2008 | Walt et al. | |
| 7,424,371 B2 | 9/2008 | Kamentsky | |
| 7,535,232 B2 | 5/2009 | Barbaro et al. | |
| 7,575,865 B2 | 8/2009 | Leamon et al. | |
| 7,645,596 B2 | 1/2010 | Williams et al. | |
| 7,782,237 B2 | 8/2010 | Ronaghi et al. | |
| 7,785,862 B2 | 8/2010 | Kim et al. | |
| 7,835,871 B2 | 11/2010 | Kain et al. | |
| 7,875,440 B2 | 1/2011 | Williams et al. | |
| 7,948,015 B2 | 5/2011 | Rothberg et al. | |
| 8,666,678 B2 | 3/2014 | Davey et al. | |
| 8,808,988 B2 | 8/2014 | Zhao et al. | |
| 10,410,739 B2 | 9/2019 | Koller et al. | |
| 11,636,922 B2 | 4/2023 | Koller et al. | |
| 2003/0219797 A1 | 11/2003 | Zhao et al. | |
| 2004/0018506 A1 | 1/2004 | Koehler et al. | |
| 2004/0197793 A1 | 10/2004 | Hassibi et al. | |
| 2004/0197845 A1 | 10/2004 | Hassibi et al. | |
| 2005/0084851 A1 | 4/2005 | Ronaghi et al. | |
| 2006/0040297 A1 | 2/2006 | Leamon et al. | |
| 2006/0147935 A1 | 7/2006 | Linnarsson | |
| 2006/0147983 A1 | 7/2006 | O'uchi et al. | |
| 2007/0059733 A1 | 3/2007 | Sundararajan et al. | |
| 2007/0059741 A1 | 3/2007 | Kamahori et al. | |
| 2007/0092872 A1 | 4/2007 | Rothberg et al. | |
| 2007/0207471 A1 | 9/2007 | Osaka et al. | |
| 2007/0219367 A1 | 9/2007 | Shchepinov et al. | |
| 2007/0281300 A1 | 12/2007 | Russell et al. | |
| 2008/0166727 A1 | 7/2008 | Esfandyarpour et al. | |
| 2008/0182757 A1 | 7/2008 | Heiner et al. | |
| 2008/0286762 A1 | 11/2008 | Miyahara et al. | |
| 2008/0286767 A1 | 11/2008 | Miyahara et al. | |
| 2009/0024331 A1 | 1/2009 | Tomaney et al. | |
| 2009/0026082 A1 | 1/2009 | Rothberg et al. | |
| 2009/0053724 A1 | 2/2009 | Roth et al. | |
| 2009/0105959 A1 | 4/2009 | Braverman et al. | |
| 2009/0127589 A1 | 5/2009 | Rothberg et al. | |
| 2009/0137404 A1 | 5/2009 | Drmanac et al. | |
| 2009/0176200 A1 | 7/2009 | Wakita et al. | |
| 2010/0035252 A1 | 2/2010 | Rothberg et al. | |
| 2010/0063743 A1 | 3/2010 | Gordon et al. | |
| 2010/0075327 A1 | 3/2010 | Maxham et al. | |
| 2010/0088255 A1 | 4/2010 | Mann | |
| 2010/0105052 A1 | 4/2010 | Drmanac et al. | |
| 2010/0137143 A1 | 6/2010 | Rothberg et al. | |
| 2010/0160172 A1 | 6/2010 | Erlich et al. | |
| 2010/0169026 A1 | 7/2010 | Sorenson et al. | |
| 2010/0173303 A1 | 7/2010 | Ronaghi et al. | |
| 2010/0188073 A1 | 7/2010 | Rothberg et al. | |
| 2010/0192032 A1 | 7/2010 | Chen et al. | |
| 2010/0197507 A1 | 8/2010 | Rothberg et al. | |
| 2010/0199155 A1 | 8/2010 | Kermani et al. | |
| 2010/0209922 A1 | 8/2010 | Williams et al. | |
| 2010/0267043 A1 | 10/2010 | Braverman et al. | |
| 2010/0282617 A1 | 11/2010 | Rothberg et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304447 A1 | 12/2010 | Harris | |
| 2010/0323348 A1 | 12/2010 | Hamady et al. | |
| 2010/0323350 A1 | 12/2010 | Gordon et al. | |
| 2011/0183320 A1 | 7/2011 | Flusberg et al. | |
| 2011/0213563 A1 | 9/2011 | Chen et al. | |
| 2011/0230358 A1 | 9/2011 | Rava | |
| 2011/0246084 A1 | 10/2011 | Ronaghi et al. | |
| 2011/0257889 A1 | 10/2011 | Klammer et al. | |
| 2011/0263463 A1 | 10/2011 | Rothberg et al. | |
| 2011/0275522 A1 | 11/2011 | Rothberg et al. | |
| 2011/0281737 A1 | 11/2011 | Rothberg et al. | |
| 2011/0281741 A1 | 11/2011 | Rothberg et al. | |
| 2011/0294115 A1 | 12/2011 | Williams et al. | |

| | | | |
|---|---|---|---|
| 2012/0035062 A1 | 2/2012 | Schultz et al. | |
| 2012/0037961 A1 | 2/2012 | Rothberg et al. | |
| 2012/0040844 A1 | 2/2012 | Rothberg et al. | |
| 2012/0109598 A1 | 5/2012 | Davey et al. | |
| 2012/0172241 A1 | 7/2012 | Rearick et al. | |
| 2012/0173158 A1 | 7/2012 | Hubbell | |
| 2012/0173159 A1 | 7/2012 | Davey et al. | |
| 2012/0264621 A1 | 10/2012 | Hubbell et al. | |
| 2013/0060482 A1 | 3/2013 | Sikora et al. | |
| 2013/0090860 A1 | 4/2013 | Sikora et al. | |
| 2014/0051584 A1 | 2/2014 | Davey et al. | |
| 2014/0274732 A1 | 9/2014 | Hanes et al. | |

FOREIGN PATENT DOCUMENTS

| | | | |
|---|---|---|---|
| EP | 2633470 | | 10/2016 |
| GB | 2461127 | | 12/2009 |
| JP | 04-262799 | | 9/1992 |
| JP | 2009527817 | A | 7/2009 |
| JP | 2013522743 | A | 6/2013 |
| WO | 1999/019717 | | 4/1999 |
| WO | 1999/057321 | | 11/1999 |
| WO | 2002/020837 | | 3/2002 |
| WO | 2002/024322 | | 3/2002 |
| WO | 2003/020895 | | 3/2003 |
| WO | 2004/001015 | | 12/2003 |
| WO | 2005/040425 | | 5/2005 |
| WO | 2007/098049 | | 8/2007 |
| WO | 2008/076406 | | 6/2008 |
| WO | 2008/092150 | | 7/2008 |
| WO | 2008/092155 | | 7/2008 |
| WO | 2009/117119 | A1 | 9/2009 |
| WO | 2009/158006 | | 12/2009 |
| WO | 2010/047804 | | 4/2010 |
| WO | 2010/077859 | | 7/2010 |
| WO | 2010/117804 | | 10/2010 |
| WO | 2010/138182 | | 12/2010 |
| WO | 2011/120964 | | 10/2011 |
| WO | 2011/156707 | | 12/2011 |
| WO | 2012/058459 | | 5/2012 |
| WO | 2012/092515 | | 7/2012 |

OTHER PUBLICATIONS

Brockman et al., "Quality scores and SNP detection in sequencing-by-synthesis systems," *Genome Research*, 18:763-770 (2008).

Chapter 2, "Machine-Learning Foundations: The Probabilistic Framework", In: Baldi, P. and Brunak, S., *Bioinformatics: The Machine Learning Approach, 2nd Edition, The MIT Press*, 47-65 (2001).

Chen et al., "The History and Advances of Reversible Terminators Used in New Geenrations of Sequencing Technology," *Genomics Proteomics Bioinformatics*, 11 :34-40 (2013).

Das, S. & Vikalo, H. Base-calling for Illumina's next-generation DNA sequencing systems via Viterbi algorithm in Allerton Conference on Communication, Control, and Computing 1733-1736 (IEEE, 2011).

Das, S. & Vikalo, H. Onlinecall : Fast online parameter estimation and base calling for illumina's next-generation sequencing, Bioinformatics 28, 1677-1683 (2012).

Das, S. & Vikalo, H. Base calling for high-throughput short-read sequencing : Dynamic programming solutions, BMC Bioinformatics 14, (2013).

Eltoukhy et al., "Modeling and Base-Calling for DNA Sequencing-By-Synthesis," *2006 IEEE International Conference on Acoustics, Speech, and Signal Processing*, vol. 2, May 2006, II-1032-II-1035.

EP communication issued in corresponding EP Application No. 14 790 898.2, issued Nov. 25, 2020.

Finotello et al., "Comparative analysis of algorithms for whole-genome assembly of pyrosequencing data," *Briefings in Bioinformatics Advance Access*, 1-12 (Oct. 21, 2011).

Gardner et al., "Rapid incorporation kinetics and improved fidelity of a novel class of 3'-PH unblocked reversible terminators," *Nucleic Acids Research*, pp. 1-12, (May 8, 2012).

Golan, D. et al., "Using state machines to model the Ion Torrent sequencing process and to improve read error rates", *Bioinfrmatics*, vol. 29. No. 13: XP055158436, Jun. 21, 2013, i344-i351.

(56)     References Cited

OTHER PUBLICATIONS

Hammond et al., "Design of a single-chip pH sensor using a conventional 0.6-μm CMOS process," *IEEE Sensors Journal*, 4:706-712 (2004).

Heer et al., "Single-chip microelectronic system to interface with living cells," *Biosensors and Bioelectronics*, 22:2546-2553 (2007).

Hert et al., "Advantages and limitations of next-generation sequencing technologies: a comparison of electrophoresis and non-electrophoresis methods," *Electrophoresis*, 29(23):4618-26 (2008).

Hizawa et al., "Fabrication of a two-dimensional pH image sensor using a charge transfer technique," *Sensors and Actuators B: Chemical*, 117:509-515 (2006).

Hughes et al., "Chemical Microsensors," *Science*, 254:74-80 (1991).

Huse et al., "Accuracy and quality of massively parallel DNA pyrosequencing," *Genome Biology*, 8(7):R143.1-R143.9 (2007).

Ji et al., "BM-BC: A Bayesian method of base calling for Solexa sequence data," *Department of Biostatistics, The University of Texas M. D. Anderson Cancer Center, Houston, Texas, U.S.A.* (http://odin.mdacc.tmc.edu/~ylji/BMBC/bmbc-ie2.pdf), 1-27, 2010.

Kao et al., "BayesCall: A model-based base-calling algorithm for high-throughput short-read sequencing," *Genome Research*, 19:1884-1895 (2009).

Langaee et al., "Genetic variation analyses by Pyrosequencing," *Mutation Research*, 573: 96-102 (2005).

Leamon et al., "Cramming More Sequening Reactions onto Microreactor Chips," *Chemical Reviews*, 107:3367-3376 (2007).

Ledergerber et al., "Base-calling for next-generation sequencing platforms," *Briefings in Bioinformatics Advance Access*, 12(5):489-497 (Jan. 18, 2011).

Loman, N.J. et al. Performance comparison of benchtop high-throughput sequencing platforms, Nature Biotechnology 30, 434-439 (2012).

Lysholm et al., "FAAST: Flow-space Assisted Alignment Search Tool," *BMC Bioinformatics 2011*, 12:293 (http://www.biomedcentral.com/1471-2105/12/293), pp. 1-7 (2011).

Margulies et al., Supplementary Methods for the article "Genome sequencing in microfabricated high-density picolitre reactors," *Nature*, 437:376-380 (2005), pp. 1-34.

Margulies et al., "Genome sequencing in microfabricated high-density picolitre reactors," *Nature*, 437:376-380 (2005).

Martinoia et al., "Development of ISFET array-based microsystems for bioelectrochemical measurements of cell populations," *Biosensors and Bioelectronics*, 16:1043-1050 (2001).

Massingham et al., "All Your Base: a fast and accurate probabilistic approach to base calling," *European Bioinformatics Institute, Wellcome Trust Genome Campus*, Hinxton, Cambridgeshire, UK (http://www.ebi.ac.uk/goldman-srv/AYB/references/ayb_revised.pdf), Oct. 26, 2011, 1-26.

Metzker, "Emerging technologies in DNA sequencing," *Genome Research*, 15:1767-1776 (2005).

Milgrew et al., "The development of scalable sensor arrays using standard CMOS technology," *Sensors and Actuators B: Chemical*, 103:37-42 (2004).

Milgrew et al., "A large transistor-based sensor array chip for direct extracellular imaging," *Sensors and Actuators B: Chemical*, 111-112:347-353 (2005).

Mir et al., "Integrated electrochemical DNA biosensors for lab-on-a-chip devices," *Electrophoresis*, 30:3386-3397 (2009).

Notification of Reasons for Refusal issued in Application No. 2016-519836, mailed Jul. 5, 2018.

PCT/US2014/059181, International Search Report and Written Opinion mailed Jan. 5, 2015, 12 pp/.

Pourmand et al., "Direct electrical detection of DNA synthesis," *Proc. Natl. Adac. Sci. U.S.A.*, 103(17):6466-6470 (2006).

Ronaghi, "Pyrosequencing Sheds Light on DNA Sequencing," *Genome Research*, 11:3-11 (2001).

Ronaghi et al., "A Sequencing Method Based on Real-Time Pyrophosphate," *Science*, 281(5375):363-365 (1998).

Svantesson et al., "A mathematical model of the Pyrosequencing reaction system," *Biophysical Chemistry*, 100:129-145 (2004).

Trojanowicz, "Recent developments in electrochemical flow detections—a review: part I. Flow analysis and capillary electrophoresis," *Anal. Chim. Acta*, 653(1):36-58 (2009).

Xu et al., "Integration of electrochemistry in micro-total analysis systems for biochemical assays: recent developments," *Talanta*, 80(1):8-18 (2009).

Yeow et al., "A very large integrated pH-ISFET sensor array chip compatible with standard CMOS processes," *Sensors and Actuators B: Chemical*, 44:434-440 (1997).

454 Sequencing System Software Manual Version 2.6 Part B : *GS Run Processor, GS Reporter, GS Run Browser, GS Support Tool*, available at http://genepool.bio.ed.ac.uk/Gene_Pool/454_software/Manuals/454SeqSys_SWManual-v2.6_PartB_May2011.pdf (last visited Aug. 31, 2012) (document dated May 2011).

Specification & Drawings of U.S. Appl. No. 61/198,222, filed Nov. 4, 2008.

Appendix to the Specification of U.S. Appl. No. 61/198,222, filed Nov. 4, 2008.

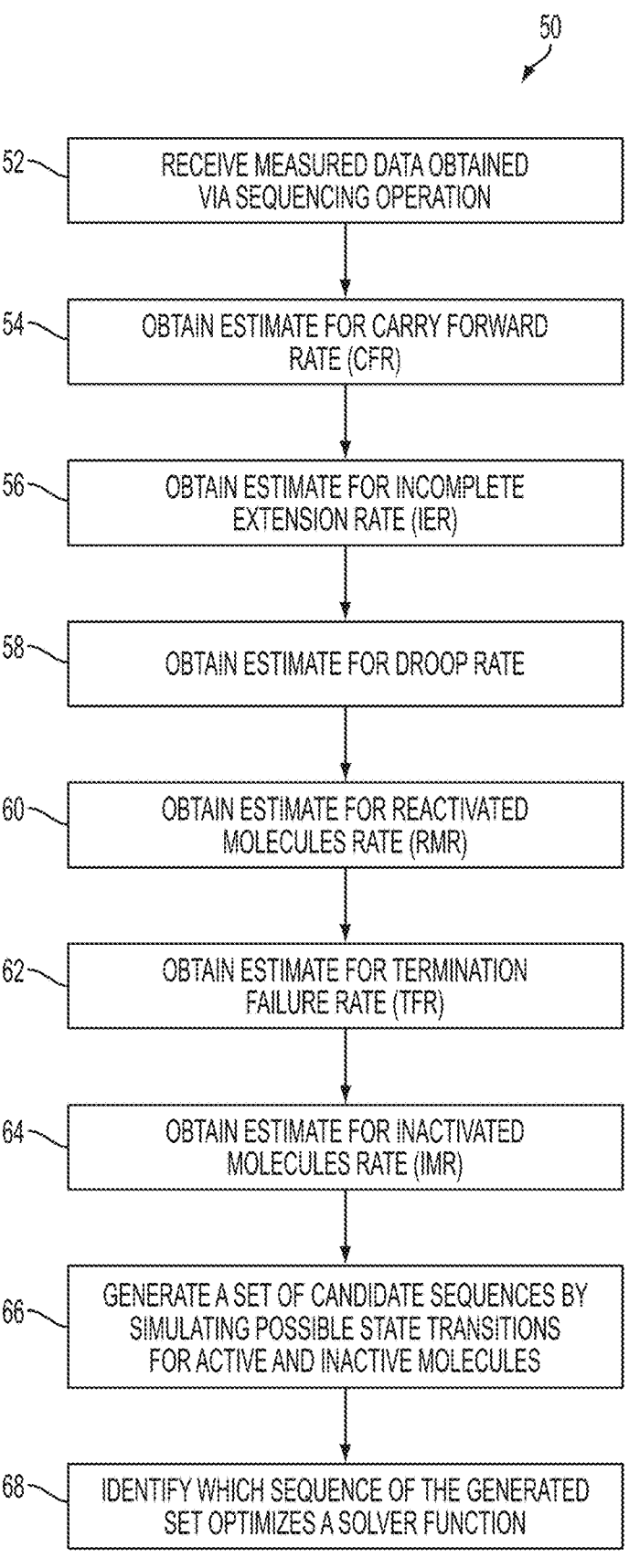

50

52 — RECEIVE MEASURED DATA OBTAINED VIA SEQUENCING OPERATION

54 — OBTAIN ESTIMATE FOR CARRY FORWARD RATE (CFR)

56 — OBTAIN ESTIMATE FOR INCOMPLETE EXTENSION RATE (IER)

58 — OBTAIN ESTIMATE FOR DROOP RATE

60 — OBTAIN ESTIMATE FOR REACTIVATED MOLECULES RATE (RMR)

62 — OBTAIN ESTIMATE FOR TERMINATION FAILURE RATE (TFR)

64 — OBTAIN ESTIMATE FOR INACTIVATED MOLECULES RATE (IMR)

66 — GENERATE A SET OF CANDIDATE SEQUENCES BY SIMULATING POSSIBLE STATE TRANSITIONS FOR ACTIVE AND INACTIVE MOLECULES

68 — IDENTIFY WHICH SEQUENCE OF THE GENERATED SET OPTIMIZES A SOLVER FUNCTION

FIG. 2

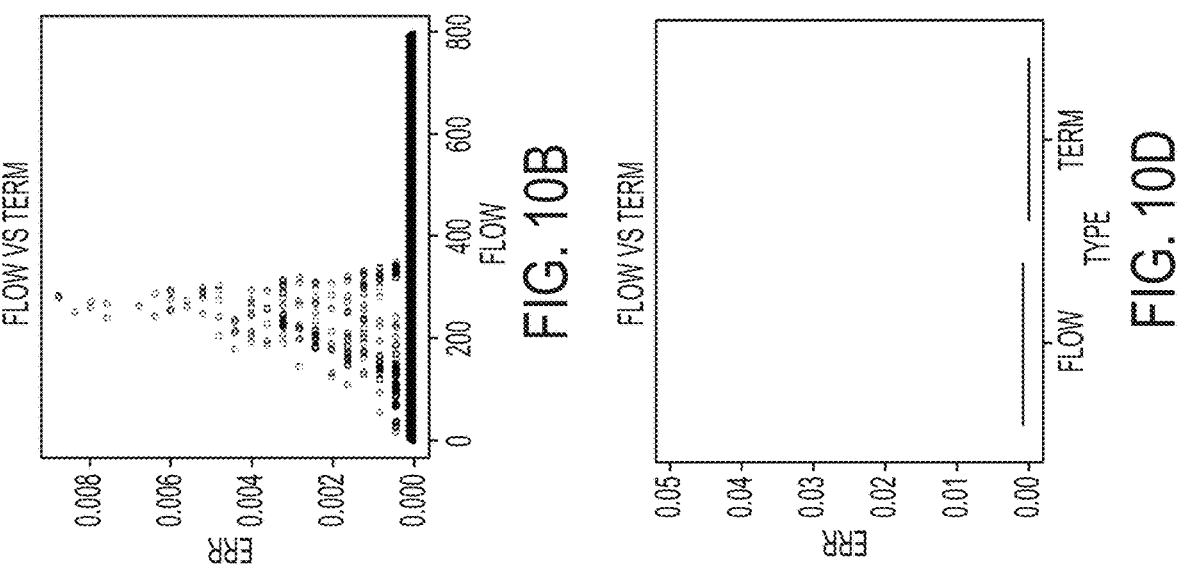
FIG. 10A
FIG. 10B
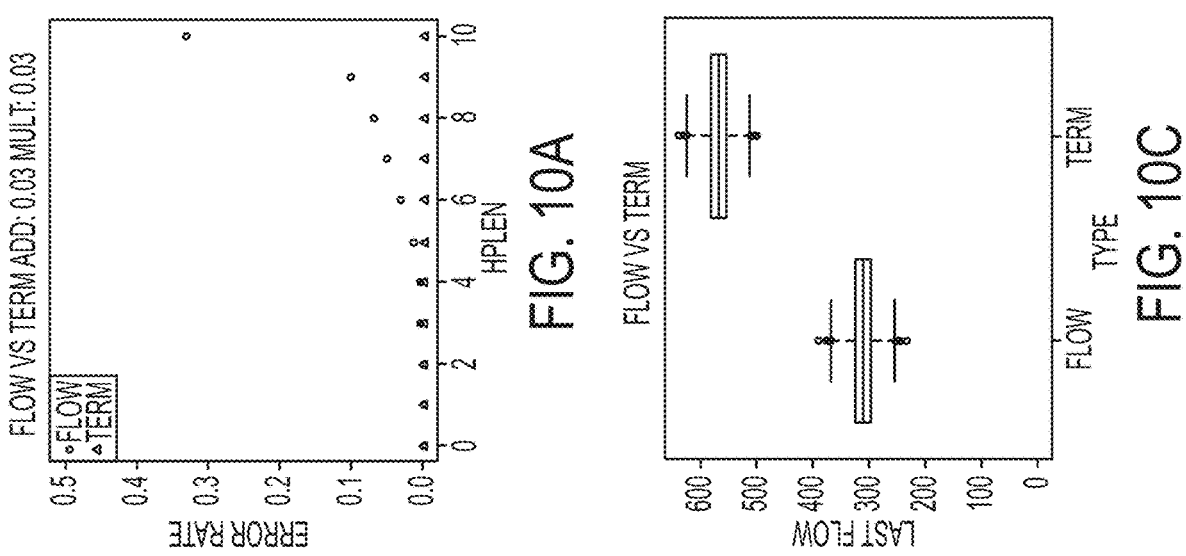
FIG. 10C
FIG. 10D

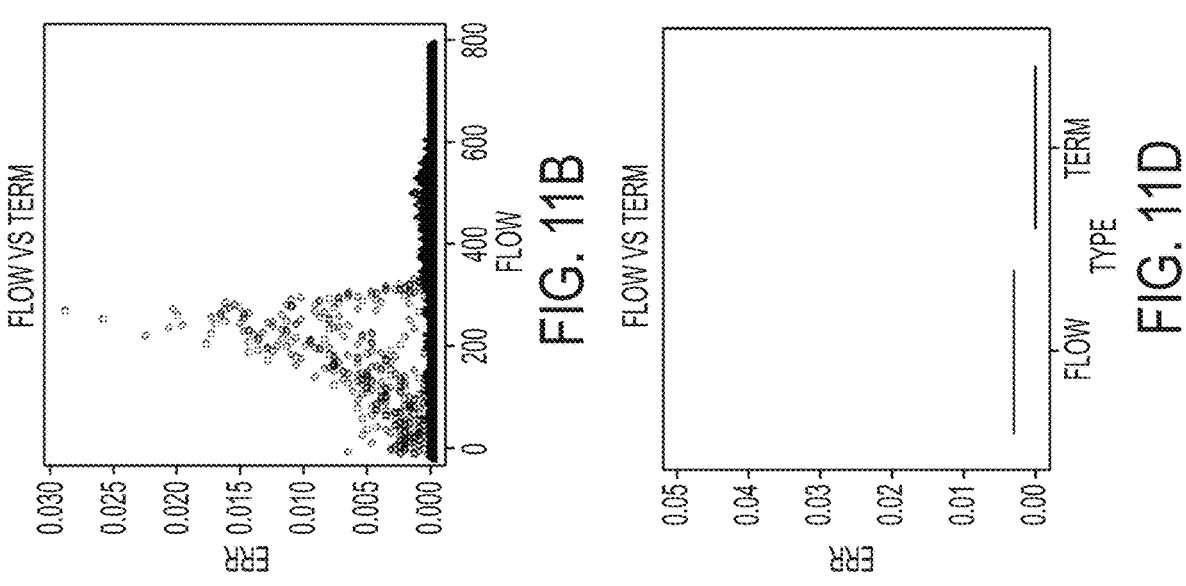
FIG. 11A
FIG. 11B
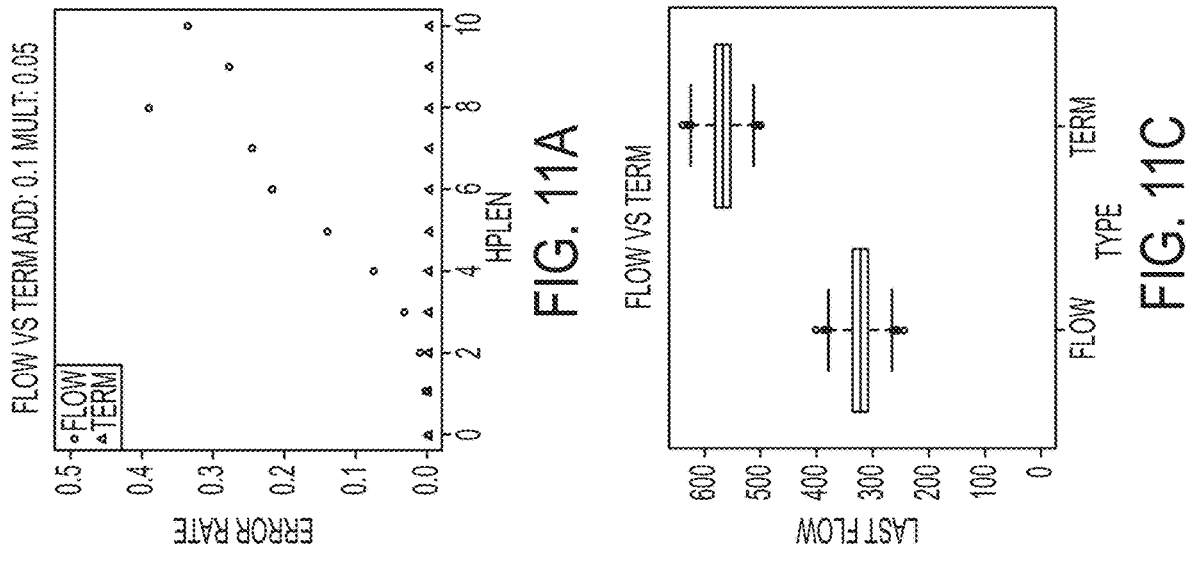
FIG. 11C
FIG. 11D

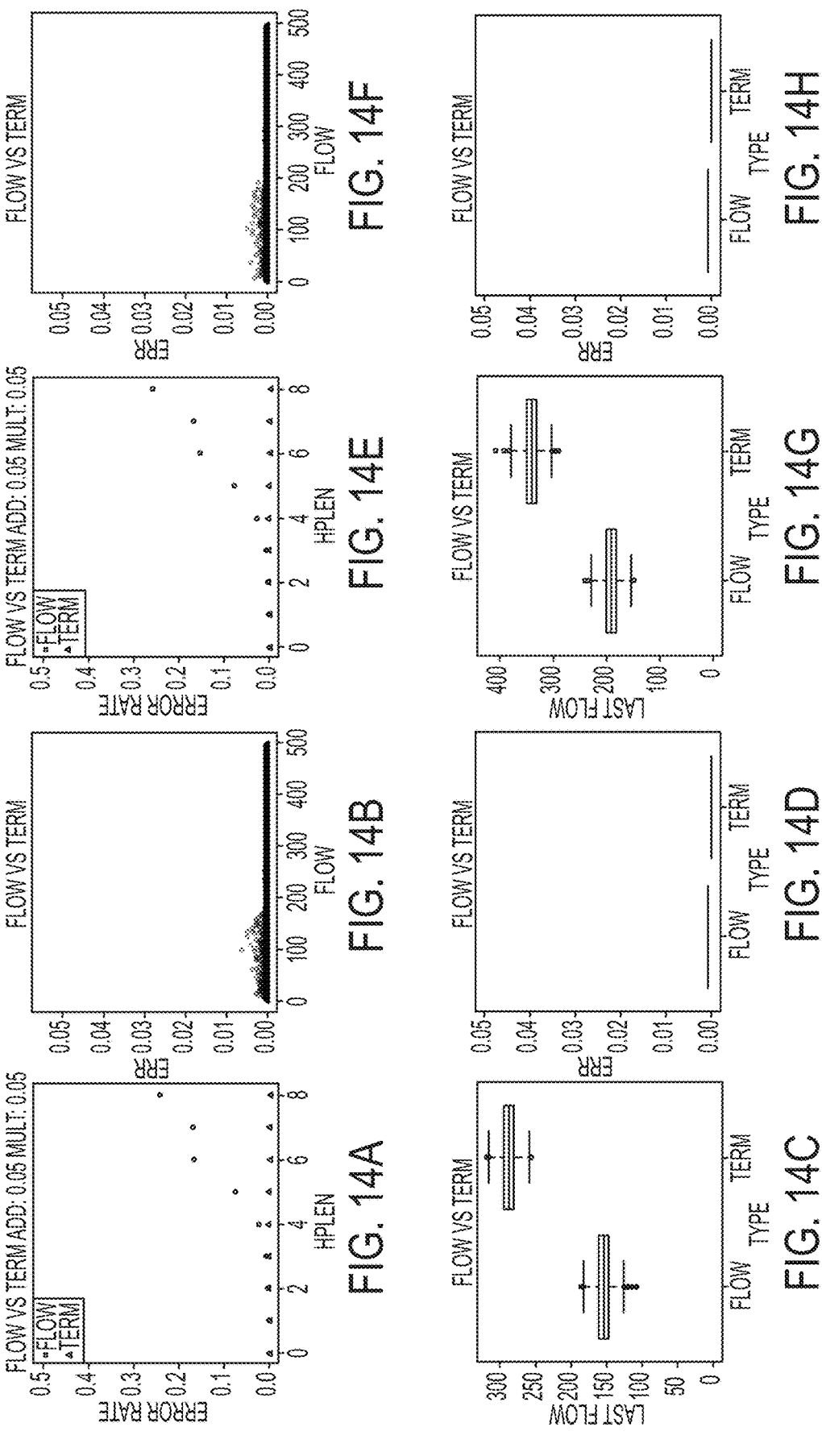

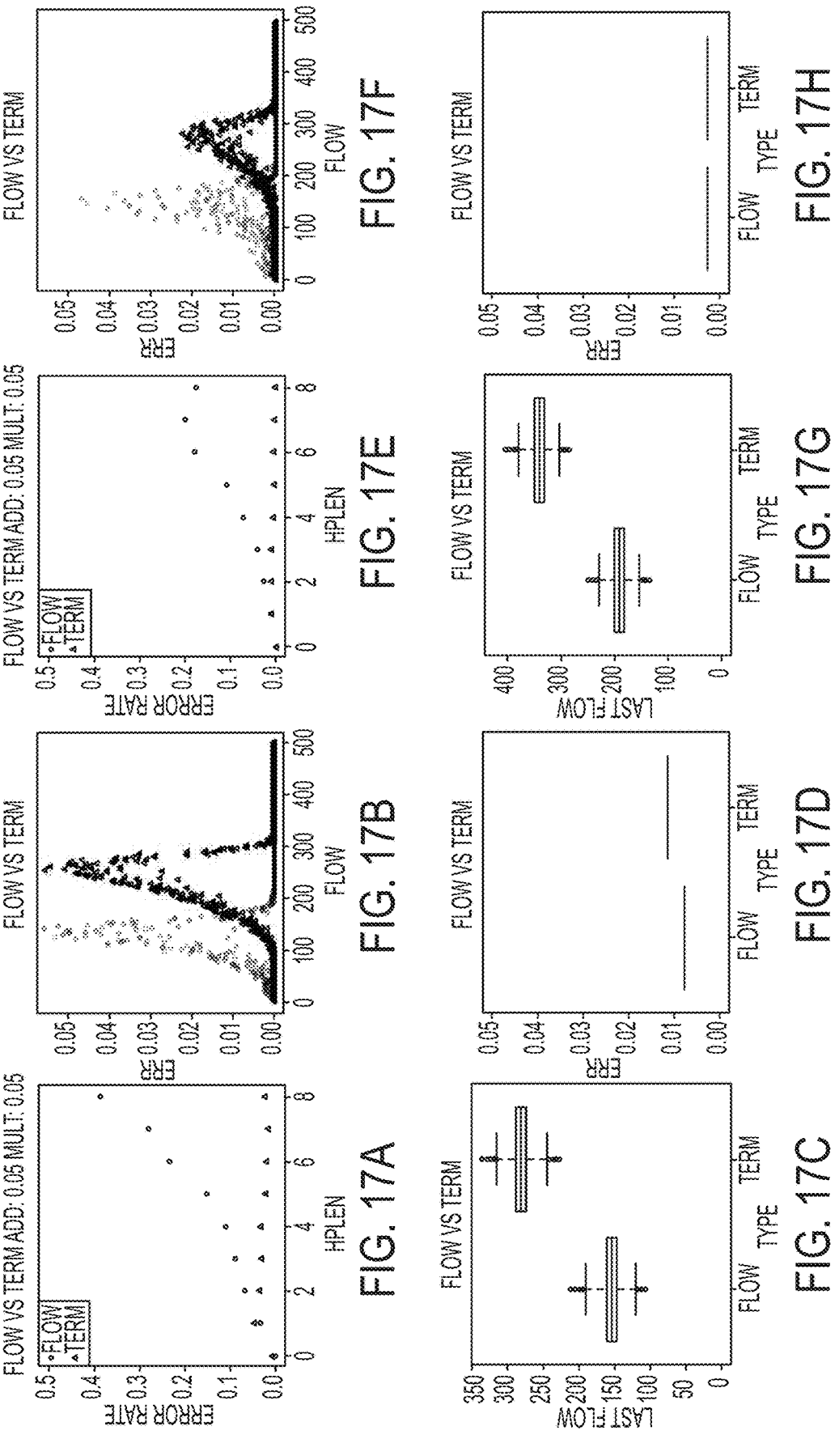

METHODS AND SYSTEMS FOR MODELING PHASING EFFECTS IN SEQUENCING USING TERMINATION CHEMISTRY

CROSS REFERENCE TO RELATED APPLICATIONS

This application is a continuation of U.S. application Ser. No. 16/55074, filed Aug. 26, 2019, which is a continuation of U.S. application Ser. No. 14/506,520, filed Oct. 3, 2014 (now U.S. Pat. No. 10,410,739), which claims priority to U.S. Provisional Application No. 61/886,878, filed on Oct. 4, 2013, each of which is hereby incorporated by reference herein in their entirety.

TECHNICAL FIELD

This application generally relates to methods, systems, and computer readable media for nucleic acid sequencing, and, more particularly, to methods, systems, and computer readable medium for modeling phasing effects in nucleic acid sequencing.

BACKGROUND

Nucleic acid sequencing, in which the order of nucleotides in a nucleic acid molecule is determined, has become ubiquitous in a wide variety of medical applications, such as biological research, genetic testing, and so forth. One type of sequencing utilized in such applications is sequencing-by-synthesis in which the order of nucleotides in a nucleic acid strand is determined by synthesizing a corresponding strand. While sequencing-by-synthesis is a high throughput method employed in many current platforms, there are several drawbacks associated with its use. For example, sequencing-by-synthesis platforms generate large volumes of sequencing data that must subsequently be processed to determine the order of the nucleotides in a given nucleic acid strand. Further, the sequencing data obtained via these methods may include a variety of errors, such as loss of phase synchrony (i.e., loss of synchronous synthesis of the identical templates), that hinder the ability to make accurate base calls. Accordingly, there exists a need for systems and methods that address these issues and enable more accurate and efficient handling of the large volumes of sequencing data obtained via the sequencing-by-synthesis platforms.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a method for nucleic acid sequencing includes receiving observed or measured nucleic acid sequencing data from a sequencing instrument configured to receive a sample nucleic acid and to process the sample nucleic acid in a termination sequencing-by-synthesis process. The method also includes generating a set of candidate sequences of bases for the observed or measured nucleic acid sequencing data by determining a predicted signal for candidate sequences using a simulation framework for simulating possible state transitions for active and inactive molecules present at a K-th base during an N-th nucleotide flow, where K and N denote indices associated with bases and nucleotide flows, respectively. The simulation framework for simulating the possible state transitions incorporates an estimated carry forward rate (CFR), an estimated incomplete extension rate (TER), an estimated droop rate (DR), an estimated reactivated molecules rate (RMR), and an estimated termination failure rate (TFR), the RMR being greater than or equal to zero and the TFR being lesser than one. The method further includes identifying, from the set of candidate sequences of bases, one candidate sequence leading to optimization of a solver function as corresponding to the sequence for the sample nucleic acid.

In accordance with at least one exemplary embodiment, a nucleic acid sequencing system includes a sequencing instrument configured to receive a sample nucleic acid, at least one nucleotide having a terminating group, a primer, and a polymerase, and to process the sample nucleic acid in a termination sequencing-by-synthesis process to produce raw nucleic acid sequencing data. A processor is configured to receive the raw nucleic acid sequencing data and to generate a set of candidate sequences of bases for sample nucleic acid by determining a predicted signal for candidate sequences using a simulation framework for simulating possible state transitions for active and inactive molecules present at a K-th base during an N-th nucleotide flow, where K and N denote indices associated with bases and nucleotide flows, respectively. The simulation framework for simulating the possible state transitions incorporates an estimated carry forward rate (CFR), an estimated incomplete extension rate (IER), an estimated droop rate (DR), an estimated reactivated molecules rate (RMR), and an estimated termination failure rate (TFR), the RMR being at a value greater than or equal to zero and the TFR being at a value lesser than one.

In accordance with at least one exemplary embodiment, an apparatus includes a machine readable memory and a processor configured to execute machine-readable instructions, the instructions which when executed cause the apparatus to receive observed or measured nucleic acid sequencing data from a sequencing instrument configured to receive a sample nucleic acid and to process the sample nucleic acid in a termination sequencing-by-synthesis process; and generate a set of candidate sequences of bases for the observed or measured nucleic acid sequencing data by determining a predicted signal for candidate sequences using a simulation framework for simulating possible state transitions for active and inactive molecules present at a K-th base during an N-th nucleotide flow, where K and N denote indices associated with bases and nucleotide flows, respectively. The simulation framework for simulating the possible state transitions incorporates an estimated carry forward rate (CFR), an estimated incomplete extension rate (IER), an estimated droop rate (DR), an estimated reactivated molecules rate (RMR), and an estimated termination failure rate (TFR), where the RMR is greater than or equal to zero and the TFR is lesser than one.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIG. 2 is a flow chart illustrating a method for identifying a nucleic acid sequence, according to an embodiment of the present disclosure.

FIGS. 10A-10D illustrate a simulated comparison of standard phasing and terminator phasing for a low noise level, according to an embodiment of the present disclosure.

FIGS. 11A-11D illustrate a simulated comparison of standard phasing and terminator phasing for a medium noise level, according to an embodiment of the present disclosure.

FIGS. 14A-14H illustrate simulated results for an incomplete extension rate of 1.5% in a termination chemistry sequencing-by-synthesis process, according to an embodiment of the present disclosure.

FIGS. 17A-17H illustrate simulated results for an incomplete extension rate of 4.5% in a termination chemistry sequencing-by-synthesis process, according to an embodiment of the present disclosure.

DETAILED DESCRIPTION

Figure 1:
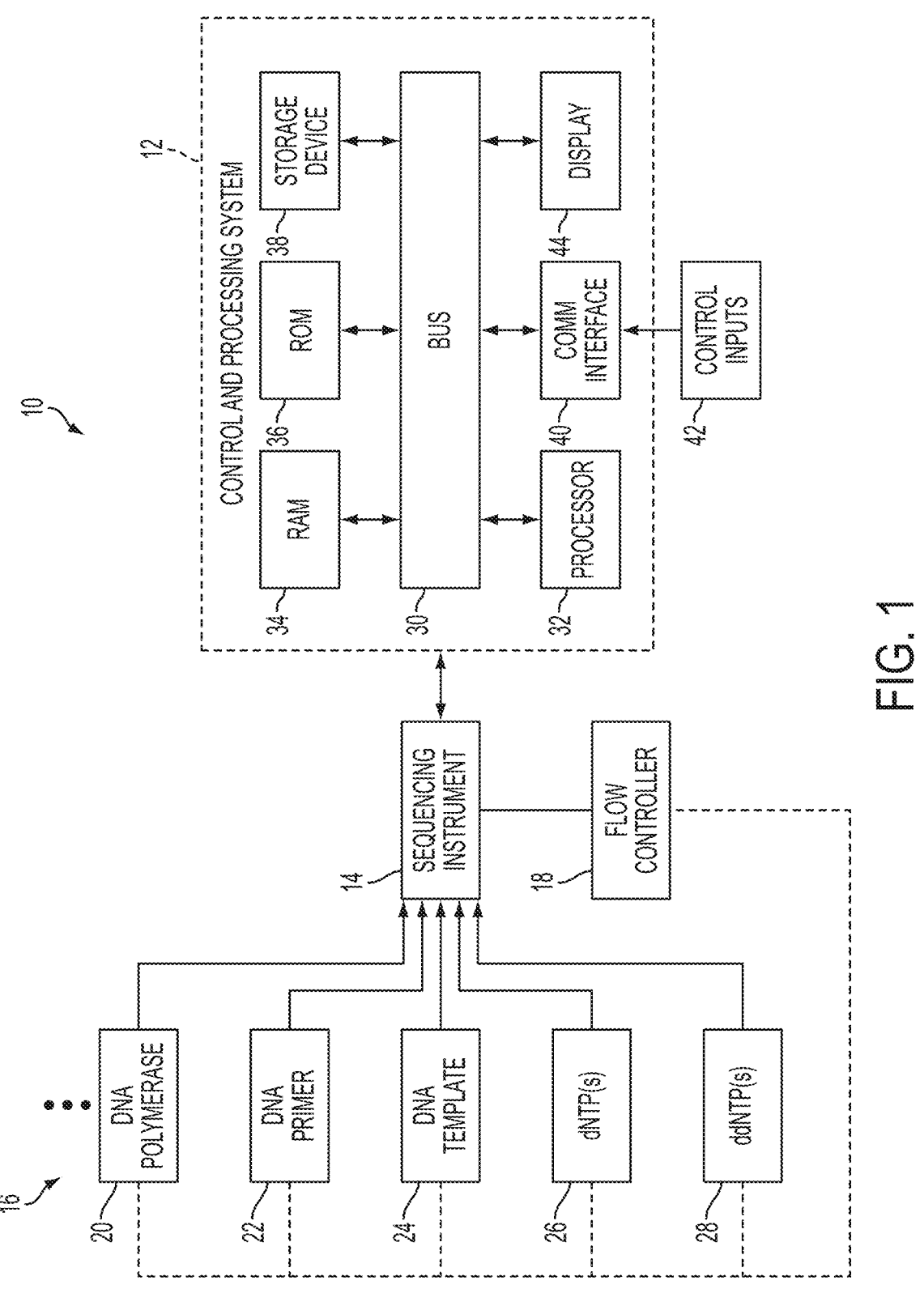
FIG. 1 is a schematic illustrating a sequencing-by-synthesis system, according to an embodiment of the present disclosure.

This description and the accompanying drawings that illustrate exemplary embodiments should not be taken as limiting. Various mechanical, compositional, structural, electrical, and operational changes may be made without departing from the scope of this description and claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In accordance with various exemplary embodiments, the present disclosure contemplates systems, methods, and computer readable media for evaluating sample nucleic acid sequences, including making base calls by processing and/or analyzing nucleic acid sequencing data that may be tainted by the presence of phasing effects capable of causing sequencing errors in a sequencing-by-synthesis process that utilizes termination chemistry. For example, in some embodiments, a solution to the sequencing problem of identifying the sequence of bases in a nucleic acid sample may be found by minimizing a distance (e.g., through a least squares fit framework) between a predicted set of values calculated under a phasing model and a measured set of values obtained via experimentation, for example, using a sequencing instrument. In some embodiments, the solution to the minimization problem may be identified by searching or traversing possible sequences with a tree-based solver. In this way, various exemplary embodiments of the present disclosure may enable base calls to be made by taking into account one or more phasing effects without the need to remove or correct for such phasing effects.

In various exemplary embodiments, the one or more phasing effects arising in the termination sequencing-by-synthesis process are captured as parameters that are estimated and provided as inputs to the phasing model. The parameters may be chosen to account for a variety of phasing errors that occur due to asynchronous synthesis among identical templates of the nucleic acid molecule to be sequenced. For example, the phasing model may incorporate parameters for incomplete extension, carry forward, droop, reactivated molecules, termination failure, and/or inactivated molecules. In this way, various exemplary embodiments may reduce or eliminate the likelihood that incorrect bases are called due to one or more phasing effects present in a termination chemistry sequencing-by-synthesis process. These and other features of various exemplary embodiments are discussed in more detail below with reference to the drawings.

FIG. 1 illustrates a nucleic acid sequencing system 10 capable of determining an order of nucleotides present in a nucleic acid sample. Polynucleotides may include the natural deoxyribonucleosides (e.g., deoxyadenosine, deoxycytidine, deoxyguanosine, and deoxythymidine for DNA or their ribose counterparts for RNA) linked by phosphodiester linkages. However, they may also include non-natural nucleotide analogs, e.g., including modified bases, sugars, or internucleosidic linkages. In an exemplary embodiment, a polynucleotide may be represented by a sequence of letters (upper or lower case), such as "ATGCCTG," and it will be understood that the nucleotides are in 5'-'3' order from left to right and that "A" denotes deoxyadenosine, "C" denotes deoxycytidine, "G" denotes deoxyguanosine, and "T" denotes deoxythymidine, and that "I" denotes deoxyinosine, and "U" denotes deoxyuridine, unless otherwise indicated or obvious from context.

The nucleic acid sequencing system 10 includes a control and processing system 12 that receives nucleic acid sequencing data from a sequencing instrument 14 for analysis and/or processing. The sequencing instrument 14 is configured to perform a sequencing-by-synthesis process using termination chemistry ("termination sequencing-by-synthesis"). As used herein, the term "termination sequencing-by-synthesis" encompasses all sequencing-by-synthesis processes that employ any type of termination chemistry. For example, termination sequencing-by-synthesis includes, but is not limited to, sequencing-by-synthesis processes in which nucleic acid replication is reversibly or irreversibly terminated in a stepwise fashion via incorporation of one or more terminators, such as chemically altered dNTPs (e.g., chemically altered dATP, dCTP, dGTP, and/or dTTP), including 2',3' dideoxynucleotides (ddNTPs) (e.g., ddATP, ddCTP, ddGTP, ddTTP) into the reaction mixture.

One or more materials 16 are provided in various concentrations under control of flow controller 18. In the illustrated embodiment, the materials include nucleic acid polymerase 20, nucleic acid primer 22, nucleic acid template 24, deoxyrobonucleotides (dNTP(s)) (e.g., dATP, dCTP, dGTP, dTTP) 26, and 2" dideoxynucleotides (ddNTPs) (e.g., ddATP, ddCTP, ddGTP, ddTTP) 28, although as discussed in detail below, the materials 16 provided for a given application may vary, for example, depending on implementation-specific considerations.

The illustrated embodiment of the control and processing system 12 includes an internal bus 30 to which a processor 32 is connected to enable communication with a variety of other system components. Control and processing system 12 also includes a random access memory (RAM), or other dynamic memory, coupled to bus 30 for storing instructions to be executed by the processor 32. The RAM 34 may also be used for storing temporary variables or other intermediate information during execution of instructions to be executed by the processor 32. Further, a read only memory (ROM) 36, or other static storage device, is provided for storing static information and instructions for the processor 32. The control and processing system 12 may also include a storage device 38, such as a magnetic disk, optical disk, or solid state drive (SSD) for storing information or instructions. The storage device 38 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. The storage device 38 may further include a computer-readable storage medium having stored therein particular computer software, instructions, or data.

The control and processing system 12 may also include a communications interface 40 that enables software and/or data to be transferred between computing system the control and processing system 12 and one or more external devices. Examples of communications interface 40 include a modem, a network interface (such as an Ethernet or other NIC card), a communications port (such as for example, a USB port, a RS-232C serial port), a PCMCIA slot and card, Bluetooth, and the like. Software and data transferred via the communications interface 40 may be in the form of signals, which can be electronic, electromagnetic, optical or other signals capable of being received by communications interface 40. These signals may be transmitted and received by communications interface 40 via a channel, such as a wireless medium, wire or cable, fiber optics, or other communications medium.

One or more control inputs 42 may be communicated to the processor 32 via the communications interface 40. Control inputs 42 may be provided via one or more input devices, such as a keyboard, an interactive display, such as an LCD display configured with touch screen input capabilities, a cursor control, such as a mouse, and so forth. Further, the processor 32 may also be coupled via bus 30 to a display 44, such as a cathode ray tube (CRT) or liquid crystal display (LCD), for displaying information to a user.

During operation of the nucleic acid sequencing system, the sequencing instrument 14 performs a termination sequencing-by-synthesis process, thereby generating raw data corresponding to an incorporation signal indicative of one or more nucleotide incorporations into a nucleic acid strand being synthesized in the sequencing operation. Further, in the illustrated nucleic acid sequencing system 10, as mentioned above, nucleic acid polymerase 20, nucleic acid primer 22, a nucleic acid template 24 to be sequenced, dNTP(s) 26, and ddNTP(s) 28 are provided as inputs to the sequencing instrument 14 for use in the termination sequencing-by-synthesis process. However, as understood by those of ordinary skill in the art, the particular type, mixture, and timing of the reactants provided to the sequencing instrument 14 will vary depending on a variety of implementation-specific considerations, such as the type of sequencing-by-synthesis method being employed, the type of termination chemistry used, the available imaging or sensing platforms, and so forth. Accordingly, the materials 16 shown in FIG. 1 are non-limiting examples of the types of reactants that could be provided to the sequencing instrument.

In various exemplary embodiments, the terminator provided to the sequencing instrument 14 may include any of a variety of classes of terminators suitable for terminating primer extension. For example, suitable terminators include irreversible terminators, such as ddNTPs that lack a 3' hydroxyl and, thus, interrupt nucleic replication by virtue of a hydrogen instead of a hydroxyl at the 3' position. As an additional example, reversible terminators also may be utilized. Such terminators may include 3'-0-blocked reversible terminators and 3'-unblocked reversible terminators. Suitable 3'-0-blocked reversible terminators may include a terminating group linked to the oxygen atom of the 3' hydroxyl of the pentose. Several commercially available terminators of this type may be utilized in different implementations, including but not limited to 3'-ONH$_2$ reversible terminators, 3'-0-allyl reversible terminators, and 3'-0-azidomethyl reversible terminators. Suitable 3'-unblocked reversible terminators include an intact 3' hydroxyl group and a terminating group linked to the base for termination of primer extension. Several commercially available terminators of this type may be utilized in different implementations, including but not limited to the 3'-OH unblocked reversible terminator named "virtual terminator" and the 3'-OH unblocked nucleotides termed "Lightening Terminators™," which have a terminating 2-nitrobenzyl moiety attached to hydroxymethylated nucleobases.

Depending on the type of terminator selected, the particular polymerase 20 selected for use in the processes performed by the sequencing instrument 14 may vary. That is, the type of nucleotide analog selected for the nucleic acid sequencing may impact the type of DNA polymerase 20 that will yield the optimal efficiency. For example, in one embodiment, the Lightening Terminators™ may be selected for use as the terminator, and the Therminator™ DNA polymerase developed for use with the Lightening Terminators™ may be utilized to optimize efficiency.

Further, depending on the type of the selected sequencing-by-synthesis process and the type of termination chemistry employed, the order and mixture of the dNTPs 26 and/or the ddNTPs 28 may be varied by the flow controller 18. For example, if a Sanger sequencing process is selected to be run by the sequencing instrument 14, four separate sequencing reactions may be run, each including one of the four types of ddNTPs and the other three dNTPs (e.g., one reaction would include ddATP, but dGTP, dCTP, and dTTP). For further example, if a dye termination sequencing process is selected to be employed by the sequencing instrument 14, the flow controller 18 may regulate a reaction including all four of the ddNTPs 28 (i.e., ddATP, ddCTP, ddGTP, ddTTP), each coupled to a different color fluorescent marker to enable identification, for example, via a fluorescent based imaging system.

According to one exemplary embodiment, the sequencing instrument 14 may be configured to perform electronic or charged-based nucleic acid termination sequencing-by-synthesis. In such an embodiment utilizing electronic or charged-based sequencing (e.g., pH-based sequencing) employing termination chemistry, an incorporation signal generated from a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid 24 may be operably associated to a primer 22 and polymerase 20. The template nucleic acid 24 may be subjected to repeated cycles or "flows" (which may be referred to herein as "nucleotide flows" from which nucleotide incorporations may result with corresponding generation of incorporation signals) of terminators and washes. In one embodiment, the terminator utilized may be one of the Lightening Terminators™, and the polymerase may be one of the Therminator™ DNA polymerase, such as Therminator III.

The primer 22 may be annealed to the sample or template 24 so that the primer's 3' end can be extended by a polymerase whenever, for example, ddNTPs 28 complementary to the next base in the template are added. Then, based on the known sequence of nucleotide flows and on measured incorporation signals during each nucleotide flow, the identity of the type, sequence and number of nucleotide(s) associated with a sample nucleic acid 24 present in a reaction chamber can be determined.

The sequence of nucleotide flows may be based on a cyclical, repeating pattern consisting of consecutive repeats of a short pre-determined cycle of nucleotide flows (e.g., consecutive repeats of pre-determined sequence of four nucleotide flows such as, for example, "ACTG . . . "); may be based in whole or in part on some other pattern of nucleotide flows (such as, e.g., any of the various nucleotide flow orders discussed or contemplated in Hubbell et al., U.S. Pat. Appl. Publ. No. 2012/0264621, published Oct. 18, 2012); or may also be based on some combination thereof.

In one embodiment, the four different kinds of ddNTPs are added sequentially to the reaction chambers, so that each reaction is exposed to the four different ddNTPs, one at a time. In an exemplary embodiment, the four different kinds of ddNTPs are added in the following sequence: ddATP, ddCTP, ddGTP, ddTTP, ddATP, ddCTP, ddGTP, ddTTP, etc., with each exposure followed by a wash step. Each exposure to a ddNTP followed by a washing step can be considered a "nucleotide flow." Four consecutive nucleotide flows can be considered a "cycle." For example, a two cycle nucleotide flow order can be represented by: ddATP, ddCTP, ddGTP, ddTTP, ddATP, ddCTP, ddGTP, ddTTP, with each exposure being followed by a wash step. In certain embodiments employing termination chemistry utilizing one or more of the terminators discussed above, each nucleotide flow may lead to a single nucleotide incorporation before primer extension is terminated.

FIG. 2 illustrates an embodiment of a method 50 for identifying a nucleic acid sequence of a DNA template. The method 50 includes receiving raw data in the form of measured or observed data obtained via a sequencing operation (block 52). For example, raw data may be received by the processor 32 of the control and processing system 12 from the sequencing instrument 14 after running a termination sequencing-by-synthesis process. The processor 32 may include a solver configured to transform the raw data received at block 52 into a base call and compile consecutive base calls associated with a sample nucleic acid template into a read, with each base call referring to a particular nucleotide identification (e.g., dATP ("A"), dCTP ("C"), dGTP ("G"), dTTP ("T")).

In order to transform this raw data into base calls, a phasing model may be generated to model the phasing effects that can occur in the termination sequencing-by-synthesis process and enable such phasing effects to be taken into account when processing or analyzing the raw data to determine the base calls. To that end, in the illustrated embodiment, an estimate of one or more of six parameters may be estimated at blocks 54, 56, 58, 60, 62, and 64.

Specifically, the method 50 can include obtaining an estimate for a carry forward rate (CFR) (block 54). The CFR may be a parameter that encompasses plus frame shifts and corresponds to the rate at which nucleic acid copies incorporate a nucleotide different from the one flown in a given flow cycle.

The method 50 also can include obtaining an estimate of an incomplete extension rate (IER) (block 56). The IER may be a parameter that encompasses minus frame shifts and corresponds to the rate at which nucleic acid copies fail to extend during a flow cycle. The method 50 further can include obtaining an estimate of a droop rate (DR) (block 58), which corresponds to a rate at which active nucleic acid copies become inactive during a cycle. The transition from active to inactive may occur, for example, due to incomplete removal of a terminating group or polymerase inactivation.

Still further, the method 50 can include obtaining an estimate for a reactivated molecules rate (RMR) (block 60). The RMR corresponds to the rate at which inactive nucleic acid copies become reactivated at a later point in time than intended. This parameter may encompass instances in which a terminating group was previously left intact and removed at a later time. Additionally, the method 50 can include obtaining an estimate for a termination failure rate (TFR) (block 62). The TFR corresponds to the rate at which phasing errors occur due to ineffective termination of primer extension. For example, in embodiments employing a 3'-unblocked reversible terminator, the TFR may include the rate at which the terminating group fails to prevent the polymerase from recognizing the 3' hydroxyl group and an additional nucleotide is therefore incorporated. The TFR may also include the rate at which the other types of terminators described in detail above fail to terminate primer extension and the rate at which a given polymerase fails to discriminate the terminating group at the 3' location, thus incorporating additional nucleotides.

In addition, the method 50 can include obtaining an estimate for inactivated molecules rate (IMR) (block 64). The IMR corresponds to the rate at which nucleic acid copies become inactive after they have incorporated a base and after the corresponding incorporation signal has been detected. Such inactivation may occur, for example, due to the use of irreversible terminators or due to a general failure of reverse termination when reversible terminators are used.

Once the estimates are obtained for the six identified parameters, or a subset of one or more of the six parameters being employed depending on the implementation, the method 50 includes generating a set of candidate sequences by simulating possible molecule state transitions for active and inactive molecules at each flow and base (block 66) and identifying which sequence of the generated set of sequences optimizes a solver function (block 68).

For example, in one embodiment, a solver may be configured as a software tool or application with functionality to efficiently solve or determine, from a set of possible or candidate sequences of bases, which sequence is in some sense most consistent with some observed or measured raw data. Possible or candidate sequences may be evaluated by predicting data that would be expected for such sequences under one or more predictive models incorporating the estimated parameters and determining how "close" under some distance criterion the predicted data are from the observed data.

To illustrate this, let Y represent observed or measured data (e.g., a vector of values such as an observed or measured ionogram or flowgram, for example, or other sequencing values), let X represent predicted data (e.g., a vector of values such as a predicted ionogram or flowgram), let A represent a set of possible or candidate nucleic acid or base sequences (e.g., the set comprising the possible sequences of A, C, G, and T; the set comprising the possible sequences of A, C, G, and T that have at most a certain length; or any other subset of candidate sequences), and let P represent a set of parameters used by the one or more predictive models (e.g., one or more of the parameters for the incomplete extension, carry-forward, droop, reactivated molecules, termination failure rates, inactivation rates). Then, in an embodiment, the solver may be thought of as a function $f$ that determines for some defined space or reaction confinement regions comprising one or more sample nucleic acids a "best" candidate sequence A* from set A such that $$A^* = f(Y, X(A, P)) = \arg_{A,P} \min D(Y - X(A, P)),$$

where $$\arg_{x,y} \min f(x,y)$$

generally denotes the value (or values) of x and y that would generally minimize the function $f(x,y)$ and where D(y−x) denotes some function of the "distance" between y and x (e.g., a sum of squared distances or any other measure of a distance between vectors, for example).

Such a solver may in principle consider the possible combinations of sequences in set A and values for the parameters in set P to identify an optimal combination of a sequence and parameter values. Of course, such an exhaustive search may be computationally expensive and potentially very time consuming. In practice, the search may advantageously be limited to a subset of sequences and subset of candidate values for the parameters. In an embodiment, the search may be facilitated by performing parameter estimation (e.g., as in blocks 54, 56, 58, 60, 62, and 64 of FIG. 2) separately from the optimization, dividing the process into two phases. For example, in a first step, the parameters may be estimated, and in a second step, the parameter estimates may be treated as fixed and supplied as inputs to the solver problem, which could then be reformulated as $$A^* = f(Y, X, A, P) = \arg_A \min D(Y - X(A|P)),$$

where X(A|P) denotes X as a function of A given some fixed parameters P.

In one embodiment, for example with P including the first five parameters (e.g., incomplete extension, carry-forward, droop, reactivated molecules, and termination failure rates represented as IER, CFR, DR, RMR, and TFR, respectively), then an optimal sequence A* may be found as follows: First, estimates of IER, CFR, DR, RMR, and TFR may be obtained using any suitable method. Reference is made to Davey et al., U.S. Pat. No. 8,666,678, filed Oct. 27, 2011, and in Davey et al., U.S. Publication No. 2014/0051584, filed Aug. 15, 2013, which are all incorporated by reference herein in their entirety, and which disclose exemplary techniques for estimating IER, CFR, and DR, with those of ordinary skill in the art understanding how such techniques may be applied to provide additional parameter estimations, for example, by using the disclosed techniques to also estimate RMR, TFR, and/or IMR. Further, in some embodiments, one or more of the parameters may be estimated separately for each cell in a dynamic programming matrix (e.g., for each cell in matrix 70, 120, and/or 130 described below), thereby resulting in variations in the estimated parameters across cells of a given matrix. In another embodiment, one or more of the parameters may be set at a fixed estimation value for a given row in the dynamic programming matrix while one or more of the remaining parameters in different columns of the matrix vary from cell to cell. Indeed, the parameter estimations for each of the cells of a matrix may vary in a variety of suitable manners, depending on the given implementation.

Second, A* may be found by solving $$A^*=\arg_A \min D(Y-X(A|IER,CFR,DR,RMR,TFR)),$$

where X(A|P) denotes X as a function of A given some fixed parameters P (e.g., IER, CFR, DR, RMR, and TFR in this example). Any suitable optimization method may be used to solve this problem, such as using a tree-based solver. Also, it should be noted that the foregoing approach can be applied using a different number or combination of the six parameters described above and the five above should be understood to be one non-limiting exemplary illustration.

Indeed, in some embodiments, a subset of the six disclosed parameters may be utilized. For instance, in one embodiment, three parameters, IER, CFR, and DR may be utilized with a termination sequencing-by-synthesis process. In another embodiment, four parameters may be utilized, for example, combining IER, CFR, DR, and RMR with TFR set to zero, or combining IER, CFR, DR, and TFR, with RMR set to zero. However, in other embodiments, the preceding five parameters may be incorporated into the model with RMR and TFR both set at values greater than zero, but with TFR less than 1. Yet another embodiment in which irreversible terminators are utilized may incorporate all of the six disclosed parameters, including IER, CFR, DR, TFR, RMR, and IMR. Indeed, the possible permutations of the parameter models provided herein enables the phasing models according to various exemplary embodiments to be applicable across a variety of sequencing platforms, including platforms that do not utilize termination chemistry. For example, in one embodiment in which termination chemistry is not employed, the five parameter model described above may collapse to a three parameter model by setting RMR to zero and TFR to one, as described in more detail below.

Figure 3:
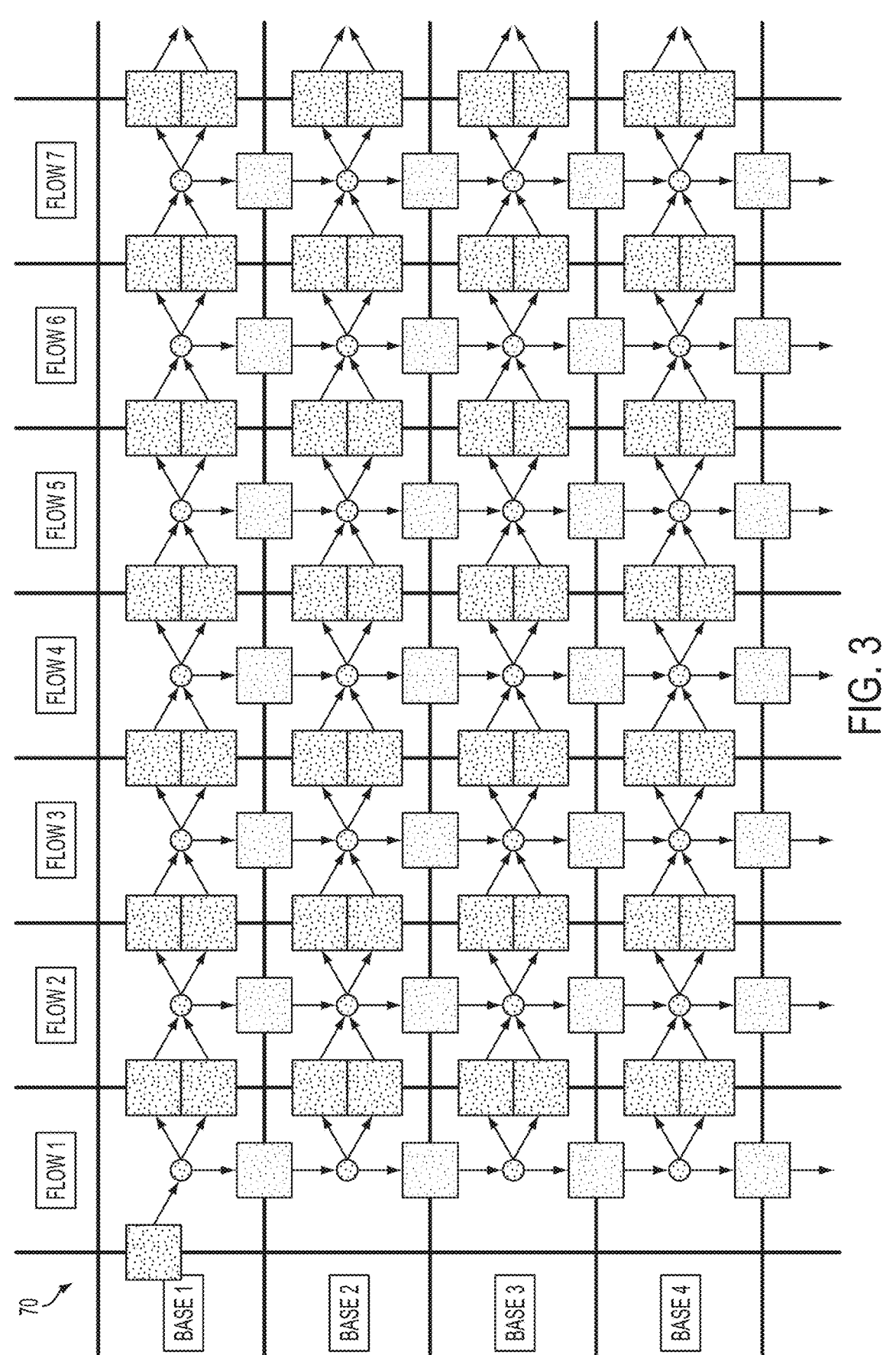
FIG. 3 is a schematic illustration of a simulation framework for calculating predicted ionograms, according to an embodiment of the present disclosure.
Figure 4:
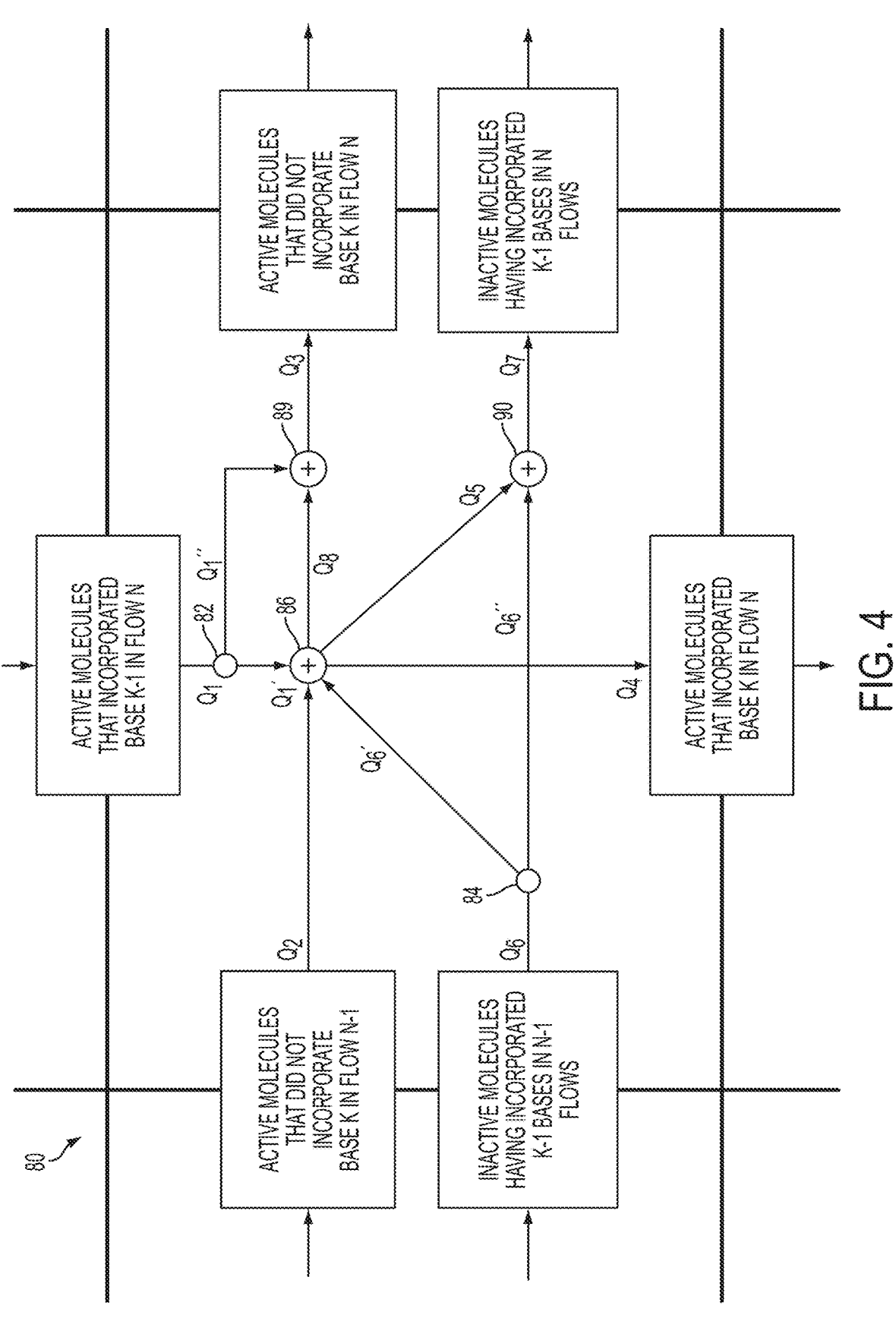
FIG. 4 illustrates an example cell within the simulation framework of FIG. 3 along with possible states and state transitions, according to an embodiment of the present disclosure.
Figure 5:
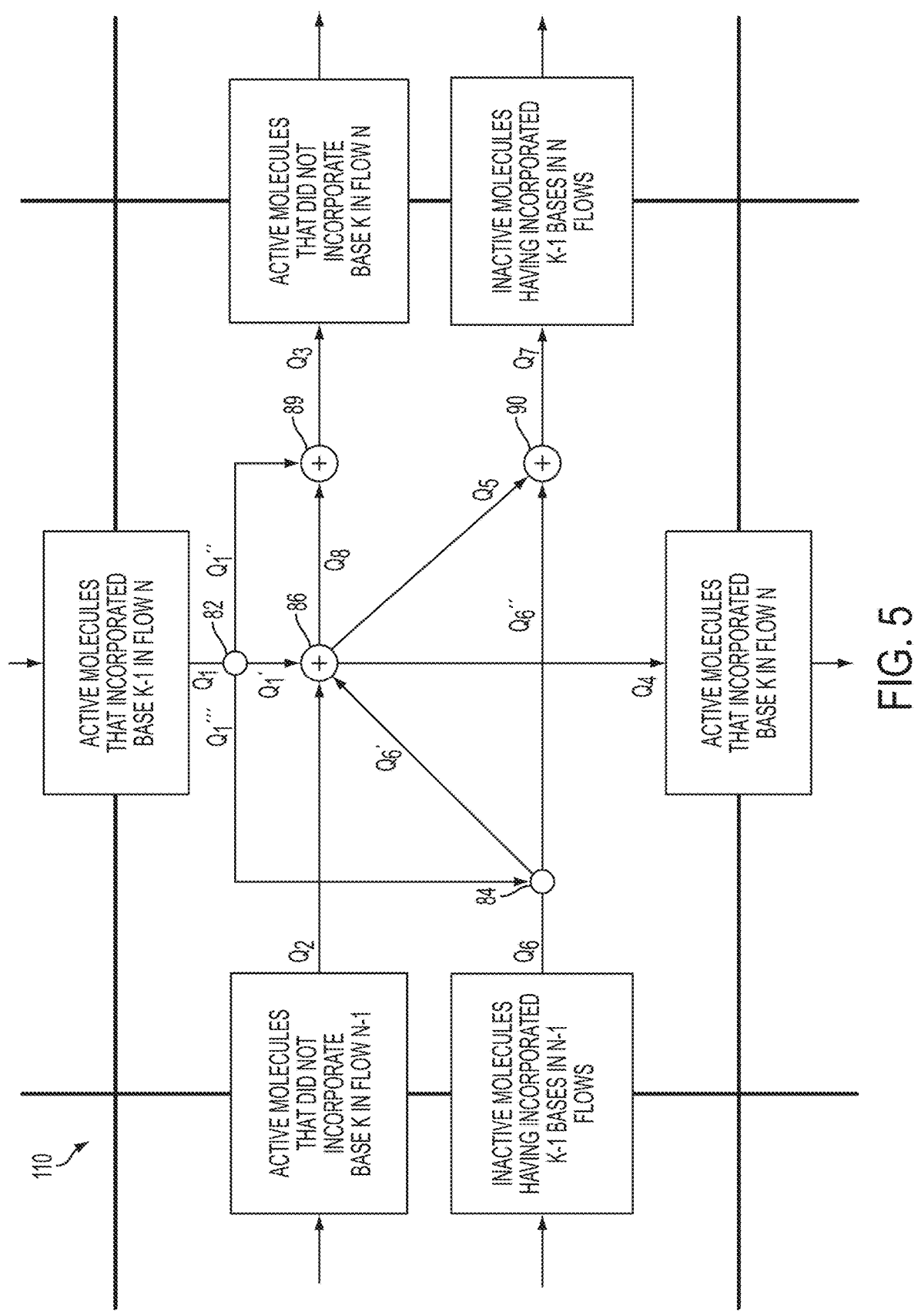
FIG. 5 illustrates an example cell within the simulation framework of FIG. 3 along with possible states and state transitions, according to another embodiment of the present disclosure.

FIGS. 3-9 illustrate exemplary embodiments of simulation frameworks and matrices that can be utilized to calculate predicted ionograms. The particular simulation framework and matrix chosen for a given application may depend on a variety of implementation-specific considerations and factors, such as, for example, the type of termination chemistry being utilized in the sequencing-by-synthesis process. For example, FIGS. 3 and 4 illustrate a simulation framework and matrix, respectively, which may be utilized to calculate predicted ionograms in a termination sequencing-by-synthesis process utilizing, for example, reversible terminators as disclosed above. For further example, FIGS. 3 and 5 illustrate a simulation framework and matrix, respectively, which may be utilized to calculate predicted ionograms in a termination sequencing-by-synthesis process utilizing, for example, irreversible terminators as disclosed above.

More specifically, FIG. 3 illustrates schematically a simulation framework 70 for calculating predicted ionograms, according to an embodiment of the present invention. The representation includes various steps and can be thought of as a matrix of the nucleotide flows (e.g., columns representing flows 1, 2, 3, and so on) and nucleotide bases (e.g., rows representing bases 1, 2, 3, and so on). Bases may or may not incorporate during a particular intended flow, and moreover may incorporate during unintended flows, as described in further detail below. Simulations of intended incorporations, incorporation failures, and/or unintended incorporations generate paths along the cells of such a matrix.

Five Parameter Phasing Model

FIG. 4 illustrates an exemplary cell 80 within the matrix illustrated in FIG. 3, with possible molecule states and state transitions labeled, according to one disclosed embodiment. Such a cell illustrates what may happen for active molecules (e.g., a molecule being actively synthesized during a flow with an active polymerase) and inactive molecules present at the K-th base during the N-th nucleotide flow in parameter phasing model incorporating the five parameters, IER, CFR, DR, RMR, and TFR. Such a phasing model may be useful in a termination sequencing-by-synthesis platform that uses reversible terminators, for example. To arrive at this point, active molecules include those that either incorporated base K−1 in flow N or did not incorporate base K in flow N−1. Inactive molecules include molecules that incorporated K−1 bases in N−1 flows.

For the active molecules that incorporated base K−1 in flow N (labeled as $Q_1$ in FIG. 4), there are then two possibilities at juncture 82. Either the terminating group failed to terminate the primer extension (e.g., $Q_1'$, which equals $Q_1 \times [TFR]$) or the termination was reversed (e.g., $Q_1''$, which equals $Q_1 - Q_1'$ or $Q_1 \times [1-TFR]$). As will be discussed further below, the $Q_1'$ subset are passed to juncture 86 where they may then undergo one of three possibilities within cell 80 (i.e., at the Kth base for flow N), and the $Q_1''$ subset is passed to juncture 89. The active molecules that enter cell 80 due to a failure to incorporate base K in the N−1 flow is represented by $Q_2$ in FIG. 4, and this subset of active molecules also is passed to juncture 86 in FIG. 4.

For the inactive molecules having incorporated K−1 bases in N−1 flows that enter cell 80 (labeled $Q_6$), those inactive molecules may either become reactivated ($Q_6'$) or remain inactive ($Q_6''$) at juncture 84. As with the other active molecules, the subset $Q_6'$ is passed to juncture 86.

Thus, arriving at juncture 86 is the sum of the active molecules ($Q_1'$, $Q_2$, and $Q_6'$) in cell 80. At juncture 86, one of three possibilities can occur. The active molecules may fail to extend or undergo incomplete extension, which subset Q8 is passed to juncture 89; they may become inactive and undergo droop, which subset $Q_5$ is passed to juncture 90; or they may undergo normal extension or a carry forward event and incorporate base K in flow N, which subset of molecules $Q_4$ becomes active molecules that have incorporated base K in flow N and move to the next cell along a flow column N.

Five Parameter Phasing Model—K-th Base Matches N-th Flow

Referring to the exemplary cell 80 within a matrix as illustrated in FIG. 4, in situations where the K-th base matches the N-th flow, the various transitions at the various junctures may be as follows: juncture 82 has one input ($Q_1$) and two outputs ($Q_1'=Q_1 \times [TFR]$ and $Q_1''=Q_1 \times [1-TFR]$); juncture 84 has one input ($Q_6$) and two outputs ($Q_6'=Q_6 \times [RMR]$ and $Q_6''=Q_6 \times [1-RMR]$; juncture 86 has three inputs ($Q_1'$, $Q_2$, and $Q_6'$) and three outputs ($Q_8=(Q_1'+Q_2+Q_6') \times ([1-IER] \times (1\ DR)]$, $Q_5=(Q_1'+Q_2+Q_6') \times [DR]$, and $Q_4=(Q_1'+Q_2+Q_6') \times ([1-IER] \times [1-DR])$); juncture 89 has two inputs ($Q_1''$ and $Q_8$) and one output ($Q_3=Q_1''+Q_8$); and juncture 90 has two inputs ($Q_5$ and $Q_6''$) and one output ($Q_7=Q_5+Q_6''$). Therefore, with respect to the outputs from the exemplary cell 80 ($Q_3$, $Q_4$, and $Q_7$), $Q_3$ may be determined directly or indirectly from prior states based on four transition factors that are based on four of the five parameters. Those transition factors are [TFR], [1−TFR], [RMR], and [IER×(1−DR)], respectively. $Q_4$ may be determined directly or indirectly from prior states based on three transition factors ([TFR], [RMR], and ([1−IER]×[1−DR])). $Q_7$ may be determined directly or indirectly from prior states based on four transition factors ([TFR], [RMR], (1−[RMR]), and [DR]).

The proportion of molecules that will remain active and not incorporate base K in flow N ($Q_3$) may be determined by multiplying some measure of the quantity (e.g., number, concentration, etc.) of molecules in the prior active states by the corresponding transition factors and adding the resulting quantities (e.g., multiplying ($Q_1'+Q_2+Q_6'$) by a transition factor [IER×(1−DR)] to obtain $Q_8$ and multiplying $Q_1$ by a transition factor [1−TFR] to obtain $Q_1''$, and adding $Q_8$ and $Q_1''$ to obtain $Q_3$). Conversely, the proportion of molecules that will remain active and incorporate base K in flow N ($Q_4$) may be determined by multiplying some measure of the quantity (e.g., number, concentration, etc.) of molecules in the active prior states by the corresponding transition factor (e.g., multiplying ($Q_1'+Q_2+Q_6'$) by a transition factor [(1−IER)×(1−DR)] to obtain $Q_4$).

Further, the proportion of molecules that will be inactive having incorporated K−1 bases in N flows ($Q_7$) may be determined by multiplying some measure of the quantity (e.g., number, concentration, etc.) of molecules in the prior active or inactive states reaching the transition by the corresponding transition factors and adding the resulting quantities (e.g., multiplying ($Q_1'+Q_2+Q_6'$) by a transition factor [DR] to obtain $Q_5$ and multiplying $Q_6$ by a transition factor [1−RMR] to obtain $Q_6''$, and adding $Q_5$ and $Q_6''$ to obtain $Q_7$).

Five Parameter Phasing Model—K-th Base Does Not Match N-th Flow

In situations where the K-th base does not match the N-th flow, the various transitions at the various junctures in FIG. 4 may be as follows: juncture 82 has one input ($Q_1$) and two outputs ($Q_1'=Q_1×$[TFR] and $Q_1''=Q_1×$[1−TFR]); juncture 86 has three inputs ($Q_1'$, $Q_2$, and $Q_6'$) and three outputs ($Q_8=$ ($Q_1'+Q_2+Q_6'$)×[(1−CFR$^M$)+CFR$^M$×IER×(1−DR)], $Q_5=$ ($Q_1'+Q_2+Q_6'$)×[CFR$^M$×DR], and $Q_4=$($Q_1'+Q_2+Q_6'$)× (CFR$^M$×[1−IER]×[1−DR])); juncture 89 has two inputs ($Q_1''$ and $Q_8$) and one output ($Q_3=Q_1''+Q_8$); juncture 84 has one input ($Q_6$) and two outputs ($Q_6'=Q_6×$[RMR] and $Q_6''=Q_6×$ [1−RMR]; and juncture 90 has two inputs ($Q_5$ and $Q_6''$) and one output ($Q_7=Q_5+Q_6''$), where M is the smallest number such that the (N−M)-th flow matches the K-th base. Therefore, with respect to the outputs from the exemplary cell 80 when the K-th base does not mat the N-th flow, $Q_3$ may be determined directly or indirectly from prior states based on four transition factors that are based on the five parameters. Those factors are [TFR], [1−TFR], [RMR], and [(1−CFR$^M$)+CFR$^M$×IER×(1−DR)]]. $Q_4$ may be determined directly or indirectly from prior states based on three transition factors ([TFR], [RMR], and (CFR$^M$×[1−IER]× [1−DR])), and $Q_7$ may be determined directly or indirectly from prior states based on four transition factors ([TFR], [RMR], (1−[RMR]), and [CFR$^M$×DR]).

For the case where the K-th based does not match the N-th flow, the proportion of molecules that will remain active and not incorporate base K in flow N (e.g., $Q_3$) may be determined by multiplying some measure of the quantity (e.g., number, concentration, etc.) of molecules in the prior active states by the corresponding transition factors and adding the resulting quantities (e.g., multiplying ($Q_1'−Q_2+Q_6'$) by a transition factor comprising term [(1−CFR$^M$)+(CFR$^M$×IER× (1−DR))], where M is the smallest number such that the (N−M)-th flow matches the K-th base, to obtain $Q_8$, and multiplying $Q_1$ by a transition factor [1−TFR] to obtain $Q_1''$, and adding $Q_8$ and $Q_1''$ to obtain $Q_3$). Conversely, the proportion of molecules that will remain active and incorporate base K in flow N ($Q_4$) may be determined by multiplying some measure of the quantity (e.g., number, concentration, etc.) of molecules in the active prior states by the corresponding transition factor (e.g., multiplying ($Q_1'−Q_2+Q_6'$) by a transition factor comprising term [CFR$^M$×(1−IER)×(1−DR)] to obtain $Q_4$). Further, the proportion of molecules that will be inactive having incorporated K−1 bases in N flows ($Q_7$) may be determined by combining the quantities (e.g., number, concentration, etc.) of molecules in the prior states by the corresponding transition factors and adding the resulting quantities (e.g., multiplying ($Q_1'−Q_2+$ $Q_6'$) by a transition factor [CFR$^M$×DR] to obtain $Q_5$ and multiplying $Q_6$ by a transition factor [1−RMR] to obtain $Q_6''$, and adding $Q_5$ and $Q_6''$ to obtain $Q_7$).

Six Parameter Phasing Model

FIG. 5 illustrates an exemplary cell 110 within the matrix illustrated in FIG. 3, with possible molecule states and state transitions labeled, according to another exemplary in which a sixth parameter is incorporated into the phasing model described in detail above. This additional parameter is an inactivated molecules rate (IMR) and corresponds to the rate at which the molecules are inactivated, which may be useful in an implementation that uses irreversible terminators or when the reversal process of reversible terminators is imperfect.

The exemplary cell 110 illustrates what may happen for active molecules (e.g., a molecule being actively synthesized during a flow with an active polymerase) and inactive molecules present at the K-th base during the N-th nucleotide flow in the six parameter model incorporating the IMR. To arrive at this point, active molecules include those that either incorporated base K−1 in flow N or did not incorporate base K in flow N−1. Inactive molecules include molecules that incorporated K−1 bases in N−1 flows.

For the active molecules that incorporated base K−1 in flow N (labeled as $Q_1$ in FIG. 5), there are then three possibilities at juncture 82. Either the terminating group failed to terminate the primer extension (e.g., $Q_1'$, which equals $Q_1$ multiplied by the termination failure rate, or $Q_1×$[TFR], the molecules were inactivated (e.g., $Q_1''$, which equals $Q_1×$[IMR]), or the termination was reversed (e.g., $Q_1'''$, which equals $Q_1−Q_1'−Q_1'''$ or $Q_1×$[1−TFR-IMR]). As will be discussed further below, the $Q_1'$ subset are passed to juncture 86, where they may then undergo one of three possibilities within cell 80 (i.e., at the Kth base for flow N), the $Q_1''$ subset is passed to juncture 89, and the $Q_1'''$ subset is passed to juncture 84. The active molecules that enter cell 80 due to a failure to incorporate base K in the N−1 flow is represented by $Q_2$ in FIG. 5, and this subset of active molecules also is passed to juncture 86 in FIG. 5.

For the inactive molecules having incorporated K−1 bases in N−1 flows that enter cell 80 ($Q_6$), those inactive molecules are combined with the inactivated molecules ($Q_6''$) at juncture 84, and the molecules at juncture 84 may then either become reactivated ($Q_6'$) or remain inactive ($Q_6''$). As with the other active molecules, the subset $Q_6'$ is passed to juncture 86.

Thus, arriving at juncture 86 is the sum of the active molecules ($Q_1'$, $Q_2$, and $Q_6'$) in cell 80. At juncture 86, one of three possibilities can occur. The active molecules may fail to extend or undergo incomplete extension, which subset $Q_8$ is passed to juncture 89; they may become inactive and undergo droop, which subset $Q_5$ is passed to juncture 90; or they may undergo normal extension or a carry forward event and incorporate base K in flow N, which subset of molecules $Q_4$ becomes active molecules that have incorporated base K in flow N and move to the next cell along a flow column N.

Six Parameter Phasing Model—K-th Base Matches N-th Flow

Referring to the exemplary cell 110 within a matrix as illustrated in FIG. 5, in situations where the K-th base matches the N-th flow, the various transitions at the various junctures may be as follows: juncture 82 has one input ($Q_1$) and three outputs ($Q_1' = Q_1 \times [TFR]$; $Q_1'' = Q_1 \times [1-TFR-IMR]$, and $Q''' = Q_1 \times [IMR]$); juncture 84 has two inputs ($Q_1'''$ and $Q_6$) and two outputs ($Q_6' = (Q_6 + Q_1''') \times [RMR]$ and $Q_6'' = (Q_6 + Q_1''') \times [1-RMR]$); juncture 86 has three inputs ($Q_1'$, $Q_2$, and $Q_6'$) and three outputs ($Q_8 = (Q_1' + Q_2 + Q_6') \times [IER \times (1-DR)]$, $Q_5 = (Q_1 + Q_2 + Q_6') \times [DR]$, and $Q_4 = (Q_1 + Q_2 + Q_6') \times ([1-IER] \times [1-DR])$); juncture 89 has two inputs ($Q_1''$ and $Q_8$) and one output ($Q_3 = Q_1'' + Q_8$); and juncture 90 has two inputs ($Q_5$ and $Q_6''$) and one output ($Q_7 = Q_5 + Q_6''$).

Therefore, with respect to the outputs from the exemplary cell 110 ($Q_3$, $Q_4$, and $Q_7$), $Q_3$ may be determined directly or indirectly from prior states using five transition factors based on five of the six parameters, the five transition factors being [IMR], [TFR], [1-TFR-IMR], [RMR], and [IER×(1-DR)]. $Q_4$ may be determined directly or indirectly from prior states based on transition factors [IMR], [TFR], [RMR], and ([1-IER]×[1-DR]). $Q_7$ may be determined directly or indirectly from prior states based on transition factors [IMR], [TFR], [RMR], (1-[RMR]), and [DR].

The proportion of molecules that will remain active and not incorporate base K in flow N ($Q_3$) may be determined by multiplying some measure of the quantity (e.g., number, concentration, etc.) of molecules in the prior active states by the corresponding transition factors and adding the resulting quantities (e.g., multiplying ($Q_1' + Q_2 + Q_6'$) by a transition factor [IER×(1-DR)] to obtain $Q_8$ and multiplying $Q_1$ by a transition factor [1-TFR-IMR] to obtain $Q_1''$, and adding $Q_8$ and $Q_1''$ to obtain $Q_3$). Conversely, the proportion of molecules that will remain active and incorporate base K in flow N ($Q_4$) may be determined by multiplying some measure of the quantity (e.g., number, concentration, etc.) of molecules in the active prior states by the corresponding transition factor (e.g., multiplying ($Q_1' + Q_2 + Q_6'$) by a transition factor [(1-TER)×(1-DR)] to obtain $Q_4$). Further, the proportion of molecules that will be inactive having incorporated K-1 bases in N flows ($Q_7$) may be determined by multiplying some measure of the quantity (e.g., number, concentration, etc.) of molecules in the prior active or inactive states reaching the transition by the corresponding transition factors and adding the resulting quantities (e.g., multiplying ($Q_1' - Q_2 + Q_6'$) by a transition factor [DR] to obtain $Q_5$ and multiplying ($Q_6 + Q_1'''$) by a transition factor [1-RMR] to obtain $Q_6'$, and adding $Q_5$ and $Q_6''$ to obtain $Q_7$).

Six Parameter Phasing Model—K-th Base Does Not Match N-th Flow

Referring to the exemplary cell 110 within a matrix as illustrated in FIG. 5, in situations where the K-th base does not match the N-th flow, the various transitions at the various junctures may be as follows: juncture 82 has one input ($Q_1$) and three outputs ($Q_1' = Q_1 \times [TFR]$, $Q_1''' = Q_1 \times [IMR]$ and $Q_1'' = Q_1 \times [1-TFR-IMR]$); juncture 84 has two inputs ($Q_1'''$ and $Q_6$) and two outputs ($Q_6' = (Q_6 + Q_1''') \times [RMR]$ and $Q_6'' = (Q_6 + Q_1''') \times [1-RMR]$); juncture 86 has three inputs ($Q_1$, $Q_2$, and $Q_6'$) and three outputs ($Q_8 = (Q_1 + Q_2 + Q_6') \times [(1-CFR^M) + CFR^M \times IER \times (1-DR)]$, $Q_5 = (Q_1' + Q_2 + Q_6') \times [CFR^M \times DR]$, and $Q_4 = (Q_1 + Q_2 + Q_6') \times ([CFR^M] \times [1-IER] \times [1-DR])$); juncture 89 has two inputs ($Q_1''$ and $Q_8$) and one output ($Q_3 = Q_1'' + Q_8$); and juncture 90 has two inputs ($Q_5$ and $Q_6''$) and one output ($Q_7 = Q_5 + Q_6''$).

Therefore, with respect to the outputs from the exemplary cell 110 ($Q_3$, $Q_4$, and $Q_7$), $Q_3$ may be determined directly or indirectly from prior states using five transition factors based on the six parameters, the five transition factors being [IMR], [TFR], [1-TFR-IMR], [RMR], and [(1-CFR^M)+ (CFR^M×IER×(1-DR)]) $Q_4$ may be determined directly or indirectly from prior states based on transition factors [IRR], [TFR], [RMR], and [CFR^M×(1-IER)×(1-DR)], and $Q_7$ may be determined directly or indirectly from prior states based on transition rates [IRR], [TFR], [RMR], [1-RMR], and [CFR^M×DR].

The proportion of molecules that will remain active and not incorporate base K in flow N ($Q_3$) may be determined by multiplying some measure of the quantity (e.g., number, concentration, etc.) of molecules in the prior active states by the corresponding transition factors and adding the resulting quantities (e.g., multiplying ($Q_1' + Q_2 + Q_6'$) by a transition factor [(1-CFR^M)+(CFR^M×IER×(1-DR)] to obtain $Q_8$ and multiplying $Q_1$ by a transition factor [1-TFR-IMR] to obtain $Q_1''$, and adding $Q_8$ and $Q_1''$ to obtain $Q_3$). Conversely, the proportion of molecules that will remain active and incorporate base K in flow N ($Q_4$) may be determined by multiplying some measure of the quantity (e.g., number, concentration, etc.) of molecules in the active prior states by the corresponding transition factor (e.g., multiplying ($Q_1' - Q_2 + Q_6'$) by a transition factor [(CFR^M)×(1-IER)×(1-DR)] to obtain $Q_4$). Further, the proportion of molecules that will be inactive having incorporated K-1 bases in N flows ($Q_7$) may be determined by multiplying some measure of the quantity (e.g., number, concentration, etc.) of molecules in the prior active or inactive states reaching the transition by the corresponding transition factors and adding the resulting quantities (e.g., multiplying ($Q_1' - Q_2 + Q_6'$) by a transition factor [CFR^M×DR]) to obtain $Q_5$ and multiplying ($Q_6 + Q_1'''$) by a transition factor [1-RMR] to obtain $Q_6''$, and adding $Q_5$ and $Q_6''$ to obtain $Q_7$).

Phasing Models when Termination Chemistry not Used

Figure 6:
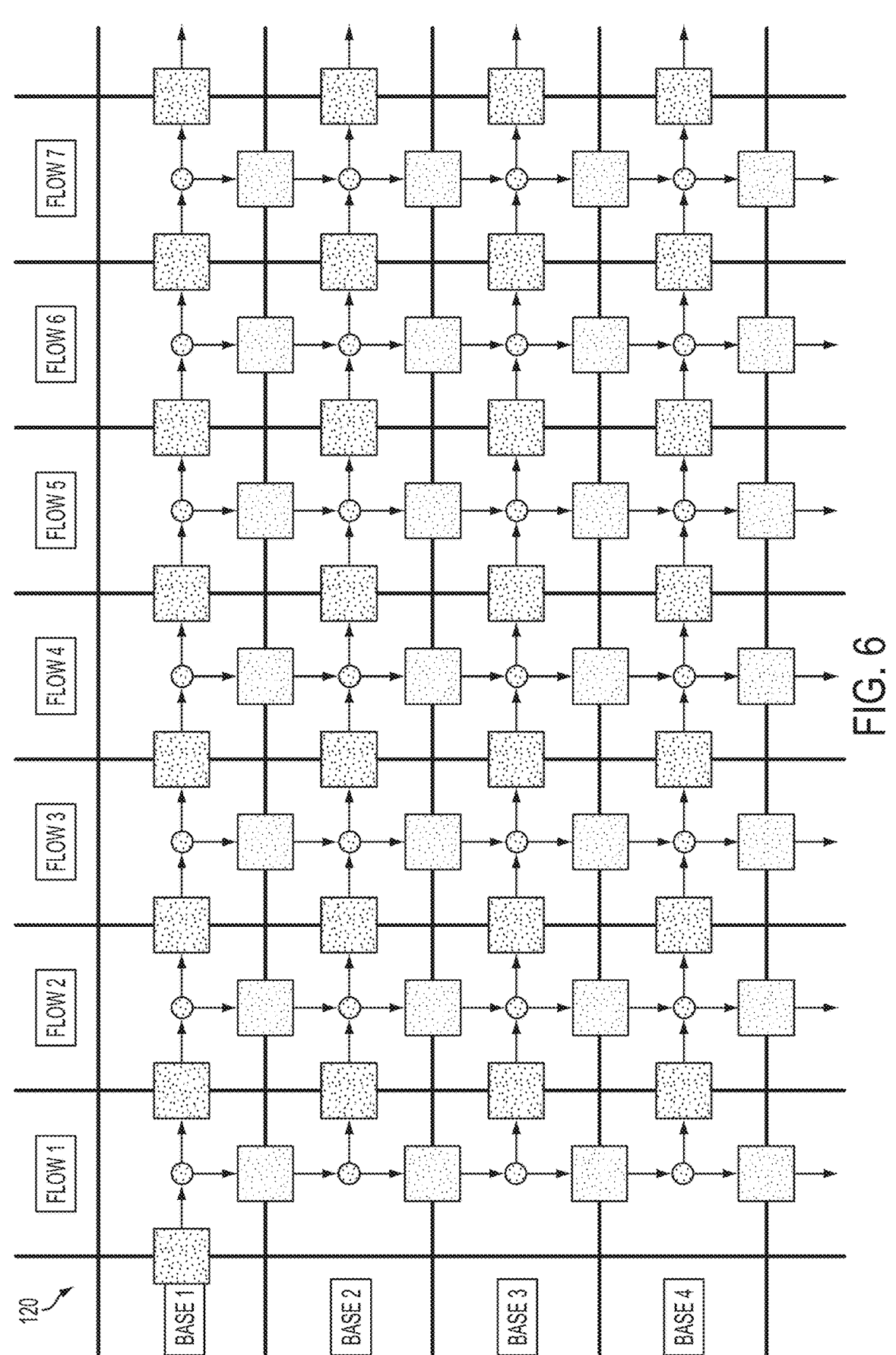
FIG. 6 illustrates a simplified schematic illustration of a simulation framework for calculating predicted ionograms, according to an embodiment of the present disclosure.

FIG. 6 illustrates schematically a simulation framework 120 for calculating predicted ionograms according to an embodiment in which termination chemistry is not utilized. In such an embodiment, for either the five or six parameters discussed above, RMR may be set to zero, and TFR may be set to one, and IMR (if being used) also may be set to zero. When the RMR is set to zero, the inactivated molecules need not be tracked because such molecules will no longer participate in any reactions. Accordingly, as before, the representation includes various steps and can be thought of as a matrix of flows (columns representing flows 1, 2, 3, and so on) and bases (rows representing bases 1, 2, 3, and so on). Again, bases may or may not incorporate in response to the flows, and simulations of incorporations (or absence thereof) generate paths along the cells of such a matrix.

Figure 7:
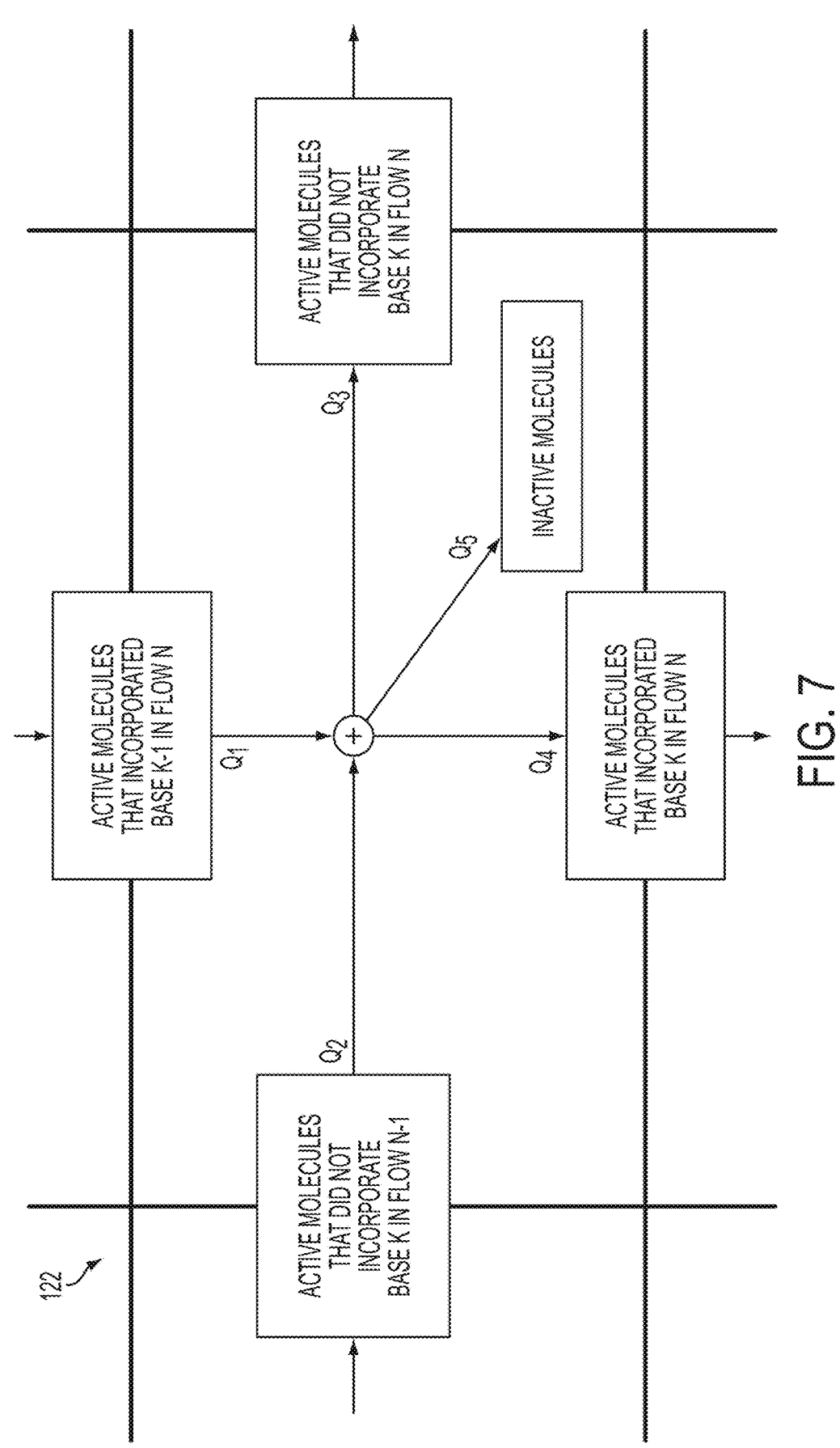
FIG. 7 illustrates an example cell within the simulation framework of FIG. 6 along with possible states and state transitions, according to an embodiment of the present disclosure.

FIG. 7 illustrates an example cell 122 within a matrix as illustrated in FIG. 6, along with possible states and state transitions according to an embodiment. Such a cell 122 illustrates what may happen for an active molecule (e.g., polymerase) present at the K-th base during the N-th flow. To arrive at this point, the molecule either incorporated base K-1 in flow N or did not incorporate base K in flow N-1. There are then several possibilities. The molecule may undergo normal extension or a carry-forward event, and incorporate base K in flow N. The molecule may also fail to extend or undergo an incomplete extension event, and not incorporate base K in flow N. Finally, the molecule may become inactive and thus undergo droop. For a population of molecules, the proportion of molecules in the possible subsequent states will depend on the incoming populations and state transition parameters.

Referring to the exemplary cell 122 within a matrix as illustrated in FIG. 7, in situations where the K-th base matches the N-th flow, the proportion of molecules that will remain active and not incorporate base K in flow N (e.g., $Q_3$) may be determined by multiplying some measure of the quantity (e.g., number, concentration, etc.) of molecules in the two prior states (e.g., $Q_1+Q_2$) by a transition factor comprising term [IER×(1−DR)], where IER is an incomplete extension rate and DR is a droop rate. Conversely, the proportion of molecules that will remain active and incorporate base K in flow N (e.g., $Q_4$) may be determined by multiplying some measure of the quantity (e.g., number, concentration, etc.) of molecules in the two prior states (e.g., $Q_1+Q_2$) by a transition factor comprising term [(1−IER)×(1−DR)].

Referring to the exemplary cell 122 within a matrix as illustrated in FIG. 7, in situations where the K-th base does not match the N-th flow, the proportion of molecules that will remain active and not incorporate base K in flow N (e.g., $Q_3$) may be determined by multiplying some measure of the quantity (e.g., number, concentration, etc.) of molecules in the two prior states (e.g., $Q_1+Q_2$) by a transition factor comprising term [(1−$CFR^M$)+($CFR^M$×IER×(1−DR))], where CFR is a carry forward rate and M is the smallest number such that the (N−M)-th flow matches the K-th base. Conversely, the proportion of molecules that will remain active and incorporate base K in flow N (e.g., $Q_4$) may be determined by multiplying some measure of the quantity (e.g., number, concentration, etc.) of molecules in the two prior states (e.g., $Q_1+Q_2$) by a transition factor comprising term [$CFR^M$×(1−IER)×(1−DR)].

Figure 8:
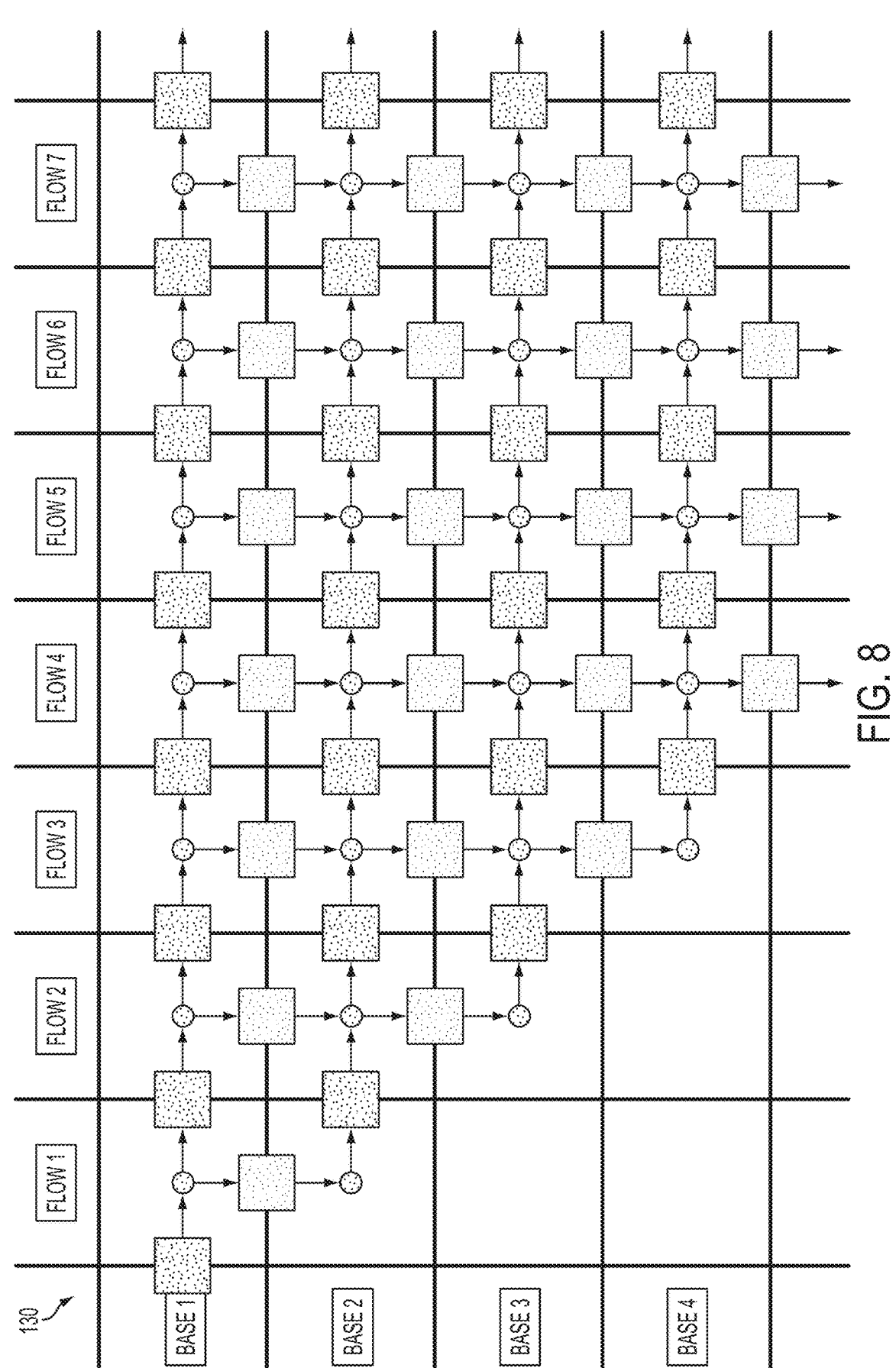
FIG. 8 illustrates a simplified schematic illustration of a simulation framework for calculating predicted ionograms, according to an embodiment of the present disclosure.

FIG. 8 illustrates schematically a simulation framework 130 for calculating predicted ionograms according to an embodiment in which the RMR rate, the TFR rate, and the IMR rate (if being modeled) are set to zero. By setting these parameters to zero, the dynamic programming matrix reduces to an upper triangular matrix as shown in FIG. 8. As in the embodiment of FIGS. 6 and 7, when the RMR is set to zero, the inactivated molecules need not be tracked because such molecules will not participate in any reactions. Accordingly, as before, the representation includes various steps and can be thought of as a matrix of flows (columns representing flows 1, 2, 3, and so on) and bases (rows representing bases 1, 2, 3, and so on). Again, bases may or may not incorporate in response to the flows, and simulations of incorporations (or absence thereof) generate paths along the cells of such a matrix.

Figure 9:
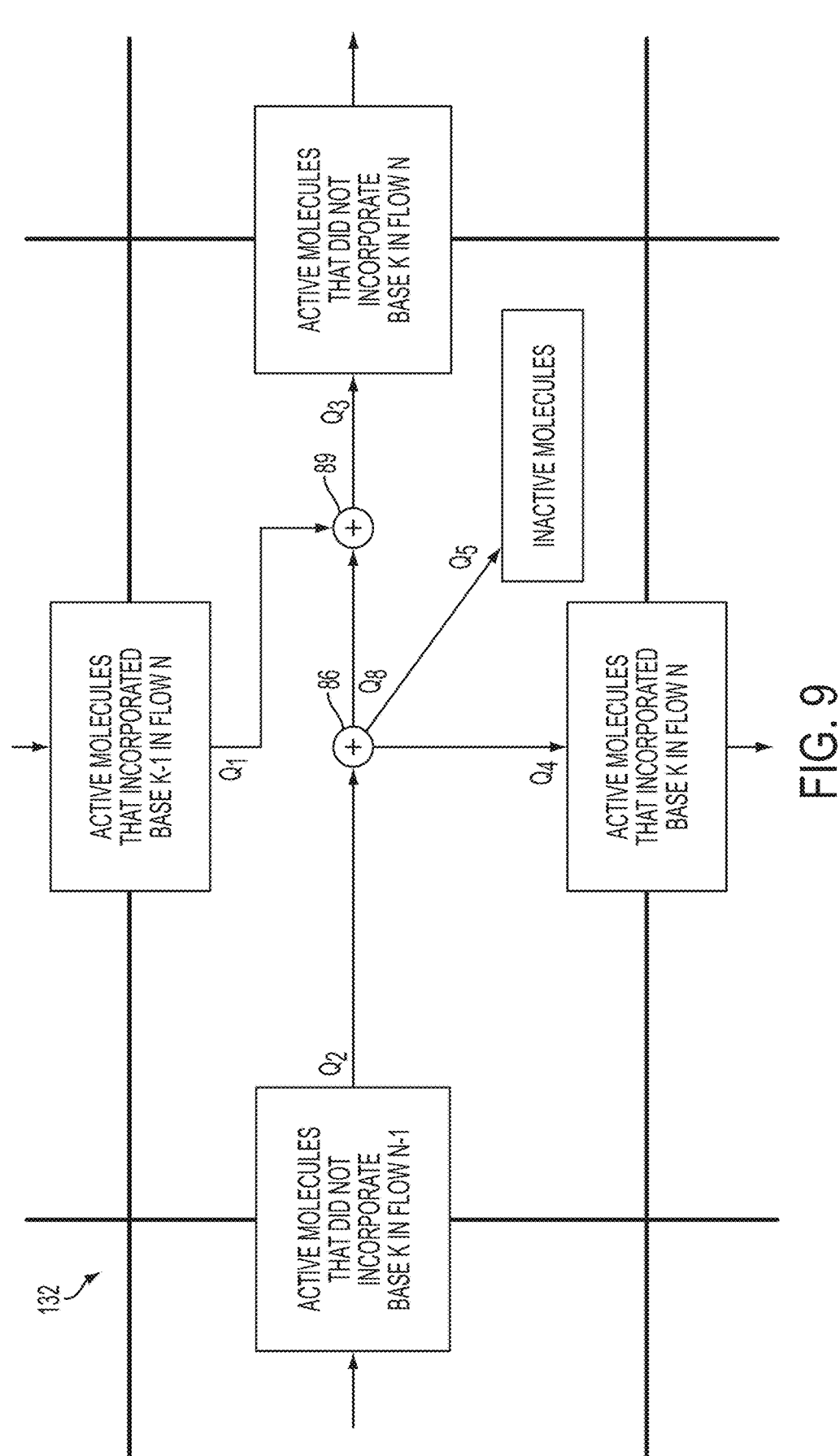
FIG. 9 illustrates an example cell within the simulation framework of FIG. 8 along with possible states and state transitions, according to an embodiment of the present disclosure.

FIG. 9 illustrates an exemplary cell 132 within the matrix illustrated in FIG. 8, with possible molecule states and state transitions labeled, according to one disclosed embodiment. Such a cell illustrates what may happen for active molecules (e.g., a molecule being actively synthesized during a flow with an active polymerase) present at the K-th base during the N-th nucleotide flow. To arrive at this point, active molecules include those that either incorporated base K−1 in flow N or did not incorporate base K in flow N−1. In this model, the active molecules that incorporated base K−1 in flow N ($Q_1$ in FIG. 9) are passed to juncture 89. The active molecules that enter cell 132 due to a failure to incorporate base K in the N−1 flow are represented by $Q_2$ in FIG. 9, and this subset of active molecules is passed to juncture 86 in FIG. 9.

At juncture 86, one of three possibilities can occur. The active molecules may fail to extend or undergo incomplete extension, which is represented by $Q_8$ in FIG. 9, and are passed to juncture 89; they may become inactive and undergo droop, which is represented by subset $Q_5$ in FIG. 9;

or they may undergo normal extension or a carry forward event and incorporate base K in flow N, which is represented by $Q_4$ in FIG. 9, which becomes active molecules that have incorporated base K in flow N and move to the next cell along a flow column N.

Referring to the exemplary cell 80 within a matrix as illustrated in FIG. 9, in situations where the K-th base matches the N-th flow, the various transitions at the various junctures may be as follows: juncture 86 has one input ($Q_2$) and three outputs ($Q_5=(Q_2)$×[IER×(1−DR)], $Q_5=(Q_2)$×[DR], and $Q_4=(Q_2)$×([1−IER]×[1−DR])); juncture 89 has two inputs ($Q_1$ and $Q_8$) and one output ($Q_3=Q_1+Q_8$).

Therefore, with respect to the outputs from the exemplary cell 80 ($Q_3$ and $Q_4$), $Q_3$ may be determined directly or indirectly from prior states based on transition rate [IER×(1−DR)], and $Q_4$ may be determined directly or indirectly from prior states based on transition rate ([1−IER]×[1−DR]). The proportion of molecules that will remain active and not incorporate base K in flow N ($Q_3$) may be determined by multiplying some measure of the quantity (e.g., number, concentration, etc.) of molecules in the prior active states by the corresponding transition factors and adding the resulting quantities (e.g., multiplying ($Q_2$) by a transition factor [IER×(1−DR)] to obtain $Q_8$, and adding $Q_8$ and $Q_1$ to obtain $Q_3$). Conversely, the proportion of molecules that will remain active and incorporate base K in flow N ($Q_4$) may be determined by multiplying some measure of the quantity (e.g., number, concentration, etc.) of molecules in the active prior states by the corresponding transition factor (e.g., multiplying ($Q_2$) by a transition factor [(1 TER)×(1−DR)] to obtain $Q_4$).

In situations where the K-th base does not match the N-th flow, the various transitions at the various junctures may be as follows: juncture 86 has one input ($Q_2$) and three outputs ($Q_8=(Q_2)$×[(1−$CFR^M$)+$CFR^M$×IER×(1−DR)], $Q_5=(Q_2)$×[DR], and $Q_4=(Q_2)$×([$CFR^M$]×[1−IER]×[1−DR]); juncture 89 has two inputs ($Q_1$ and $Q_8$) and one output ($Q_3=Q_1+Q_8$). Therefore, with respect to the outputs from the exemplary cell 80 ($Q_3$ and $Q_4$), $Q_3$ may be determined directly or indirectly from prior states based on transition factor [(1−$CFR^M$)+$CFR^M$×IER×(1−DR)], and $Q_4$ may be determined directly or indirectly from prior states based on transition factor ([$CFR^M$]×[1−IER]×[1−DR]). The proportion of molecules that will remain active and not incorporate base K in flow N ($Q_3$) may be determined by multiplying some measure of the quantity (e.g., number, concentration, etc.) of molecules in the prior active states by the corresponding transition factors and adding the resulting quantities (e.g., multiplying ($Q_2$) by a transition factor [(1−$CFR^M$)+$CFR^M$× IER×(1−DR)] to obtain $Q_8$, and adding $Q_8$ and $Q_1$ to obtain $Q_3$). Conversely, the proportion of molecules that will remain active and incorporate base K in flow N ($Q_4$) may be determined by multiplying some measure of the quantity (e.g., number, concentration, etc.) of molecules in the active prior states by the corresponding transition factor (e.g., multiplying ($Q_2$) by a transition factor [$CFR^M$×(1−IER)×(1− DR)] to obtain $Q_4$).

Simulation Studies

FIGS. 10A-10D, 11A-11D, and 12A-12D illustrate simulated plots showing a comparison between the termination chemistry phasing models using the five parameters IER, CFR, DR, RMR, and TFR disclosed herein (shown by triangles and abbreviation "term" in figures) and standard phasing models utilized for sequencing systems that do not employ termination chemistry (shown by circles and abbreviation "flow" in figures), both having the same simulated phasing errors. The embodiment detailed in FIGS. 6 and 7 was used to simulate standard phasing while the embodiment detailed in FIGS. 8 and 9 was used to simulate termination chemistry phasing. In the simulations presented, RMR was set to zero and TFR to less than 1. FIGS. 10A-10D illustrate plots showing the simulated results for a low noise level (with the noise standard deviations set at 0.03 additive, 0.03 multiplicative); FIGS. 11A-11D illustrate plots showing the simulated results for a medium noise level (with the noise standard deviations set at 0.1 additive, 0.05 multiplicative); and FIGS. 12A-12D illustrate plots showing the simulated results for a high noise level (with the noise standard deviations set at 0.2 additive, 0.05 multiplicative). As shown in the following figures, when experiencing the same phasing parameters, the termination chemistry model exhibits reduced error rates per flow as compared to the standard model. Further, based on the simulations presented, the termination chemistry models provided herein enable unexpected and significantly greater accuracy in the results for longer homopolymers.

Figure 12A:
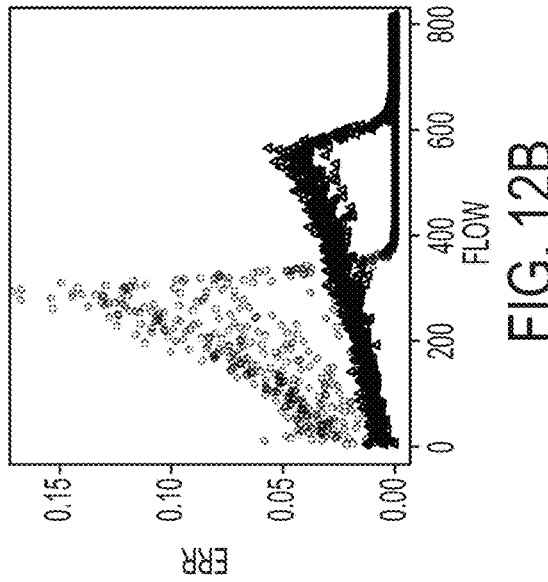
FIGS. 12A-12D illustrate a simulated comparison of standard phasing and terminator phasing for a high noise level, according to an embodiment of the present disclosure.
Figure 12B:
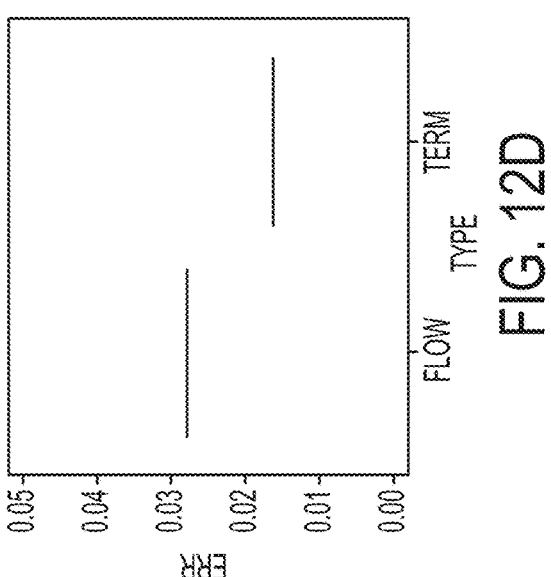
Figure 12C:
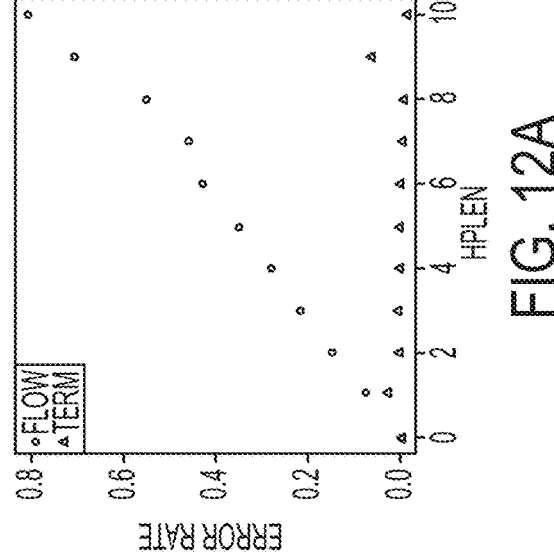
Figure 12D:
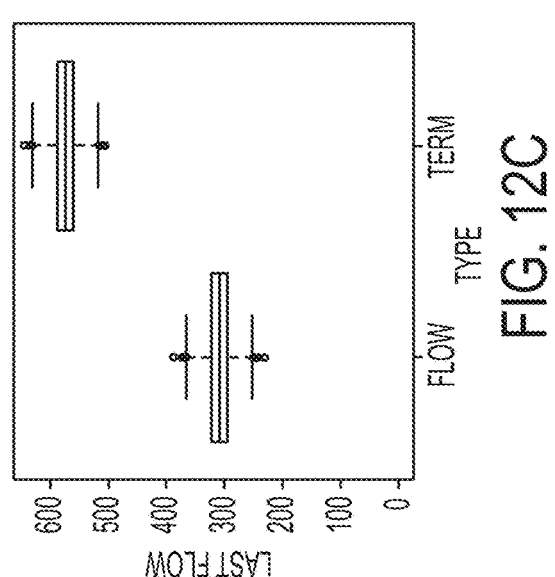

Specifically, FIGS. 10A, 11A, and 12A illustrate an error rate versus homopolymer length for low, medium, and high noise levels, respectively. As shown in these plots, the termination chemistry error rate is significantly reduced compared to the standard error rate at each of the noise levels. FIGS. 10B, 11B, and 12B illustrate an error rate by flow for low, medium, and high noise levels, respectively. As shown in these plots, the termination chemistry models provided herein enable reduced errors rates per flow. FIGS. 10C, 11C, and 12C illustrate the number of flows it takes to sequence through the template for the low, medium, and high noise levels, respectively. FIGS. 10D, 11D, and 12D illustrate the average error rates per base for the low, medium, and high noise levels, respectively, again showing the reduction in error rates with the termination chemistry model.

Figures 13A, 13B, 13C, 13D, 13E, 13F, 13G, 13H:
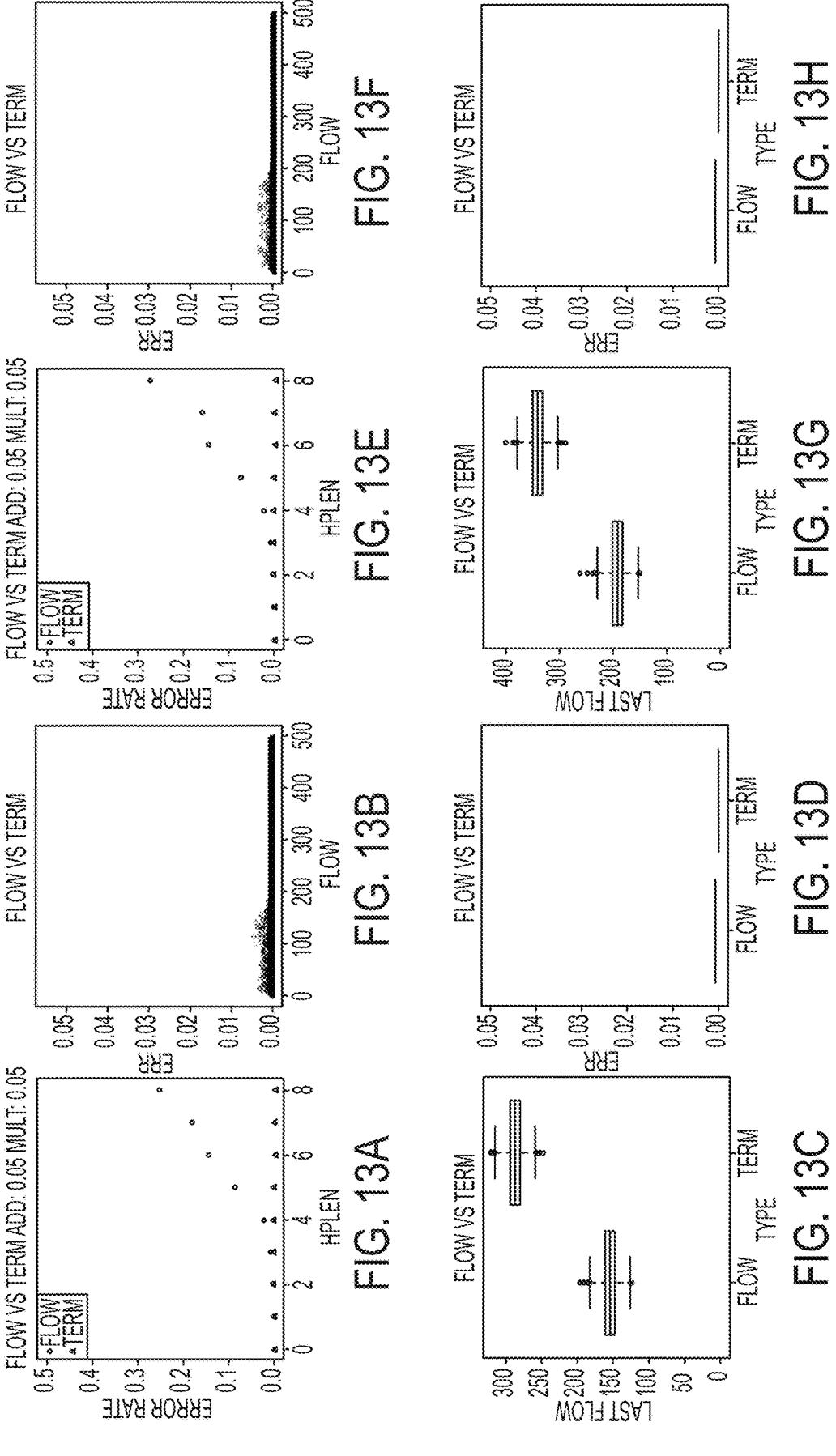
FIGS. 13A-13H illustrate simulated results for an incomplete extension rate of 0.5% in a termination chemistry sequencing-by-synthesis process, according to an embodiment of the present disclosure.
Figures 15A, 15B, 15C, 15D, 15E, 15F, 15G, 15H:
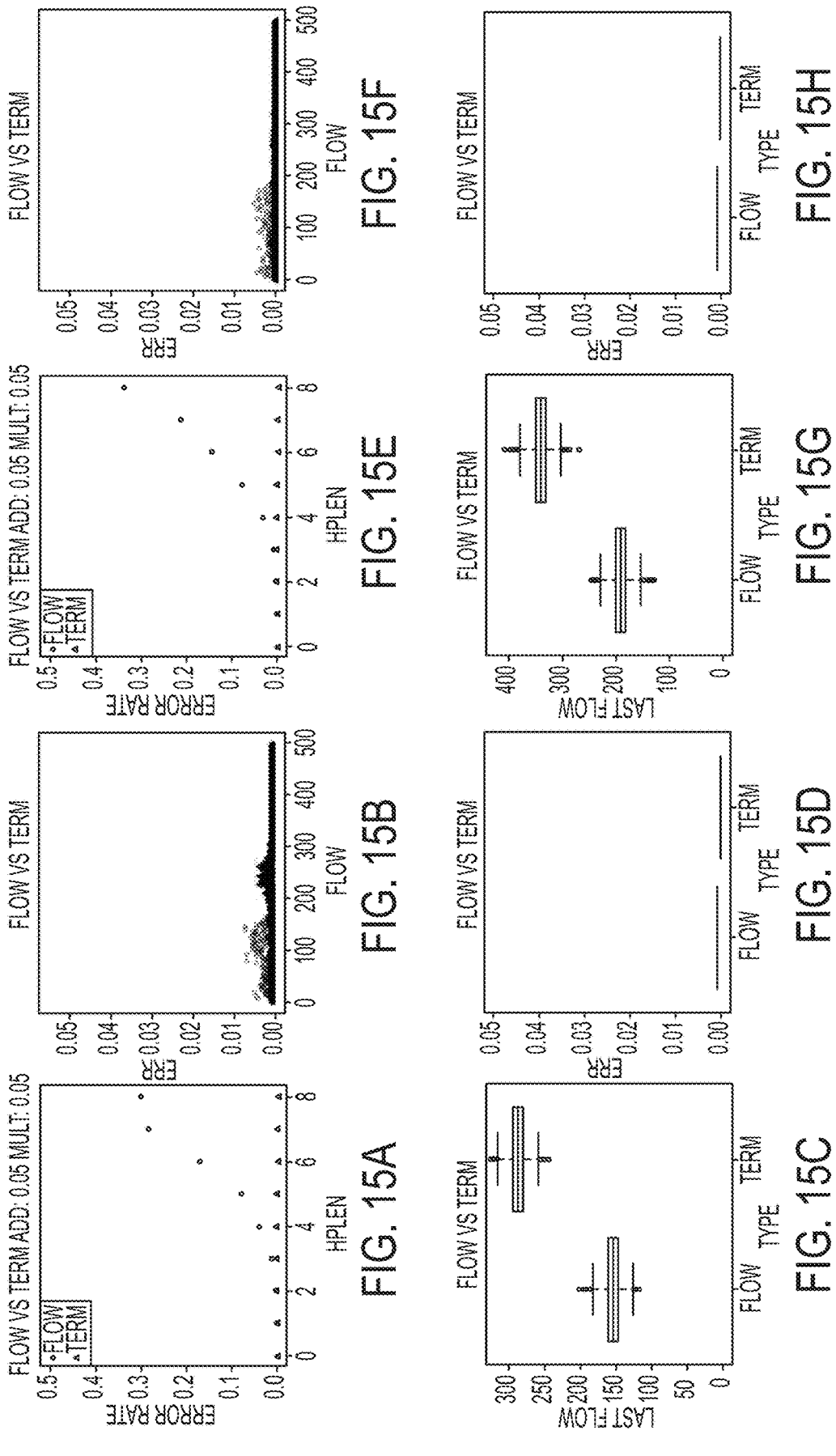
FIGS. 15A-15H illustrate simulated results for an incomplete extension rate of 2.5% in a termination chemistry sequencing-by-synthesis process, according to an embodiment of the present disclosure.
Figures 16A, 16B, 16C, 16D, 16E, 16F, 16G, 16H:
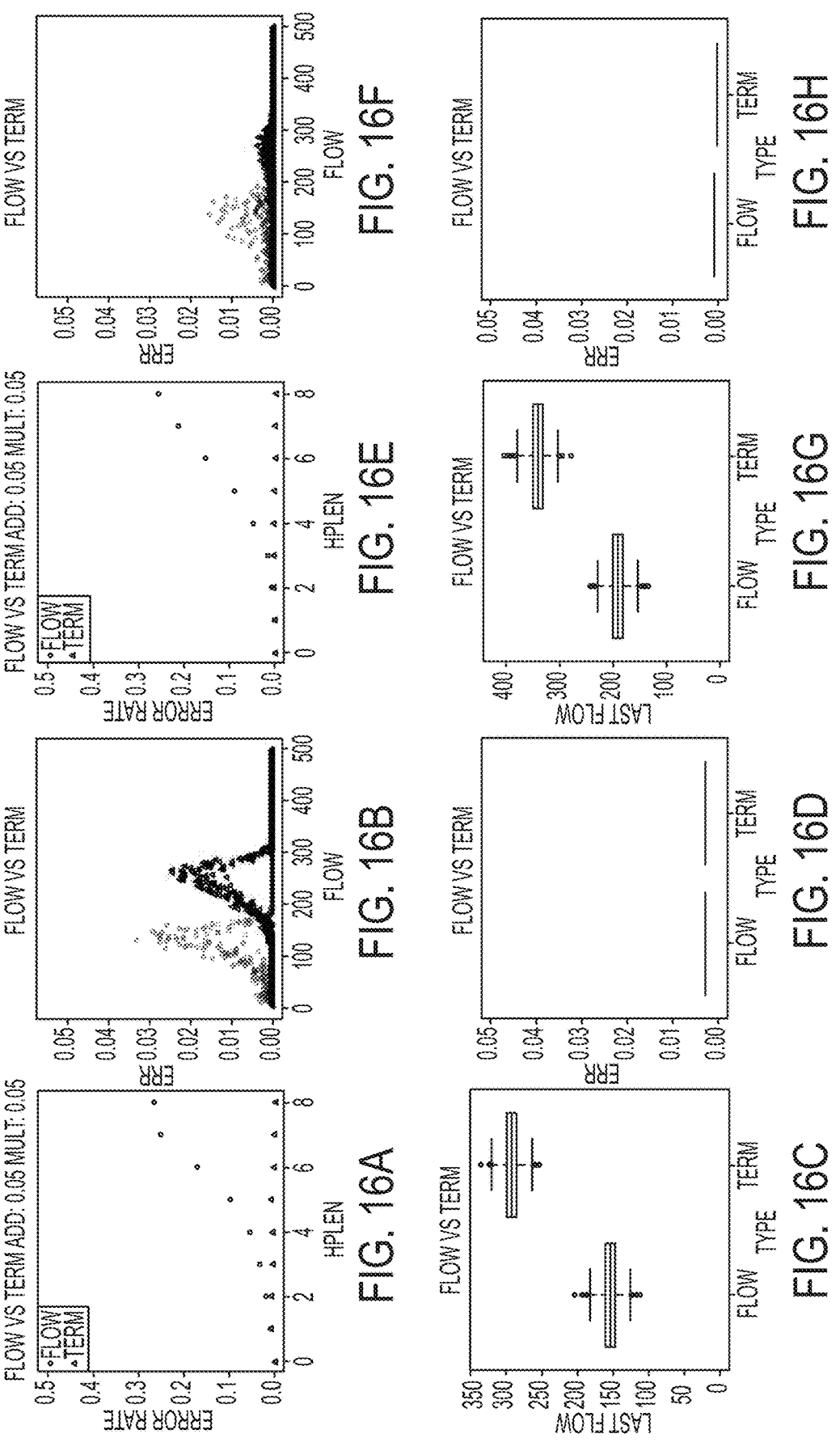
FIGS. 16A-16H illustrate simulated results for an incomplete extension rate of 3.5% in a termination chemistry sequencing-by-synthesis process, according to an embodiment of the present disclosure.

FIGS. 13A-13H, FIGS. 14A-14H, FIGS. 15A-15H, FIGS. 16A-16H, and FIGS. 17A-17H illustrate simulations comparing termination chemistry modeling and standard modeling for incomplete extension levels of 0.5, 1.5, 2.5, 3.5, and 4.5, respectively. Sets A-D and E-F simulate the same set of base sequences and phasing parameters for different nucleotide flow orders. The noise standard deviations were set at 0.05 additive, 0.05 multiplicative. As shown in the illustrated simulations, the termination chemistry model offers improved error rates for longer homopolymer lengths, as can be seen from FIGS. 13A,E, 14A,E, 15A,E, 16A,E. Phasing effects accumulate over time so that later flows in general experience larger error rates than earlier flows. Even though using termination chemistry requires more total flows to sequence through a template sequence of a given length (see FIGS. C), the simulated peak error rate per flow (which always occurs in the later flows, towards the end of the template) does not exceed and generally stays significantly below the simulated peak error rate for non-terminator sequencing. The observed simulated error rates vary with the nucleotide flow order. For example, in FIG. 16B, the error peak for the termination chemistry model occurs at a later point than the error peak for the standard model and is lower in height. A similar effect is realized in FIGS. 17B and 17F in which the error rate remains low for the termination model for more flows than the standard model. In FIGS. 13D,H-17D,H (with the exception of 17D) the termination chemistry model simulated results indicate lower per base error rates and thus higher overall base accuracy.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the claims being entitled to their full breadth and scope, including equivalents.

What is claimed is:

1. A method for nucleic acid sequencing, comprising:
obtaining raw sequencing data, the raw sequencing data based on detecting signal emission during incorporation of one or more nucleotide species in response to a nucleotide flow during a sequencing reaction for sequencing a sample nucleic acid comprising a total number of nucleotide flows of greater than 160, wherein the raw sequencing data comprises one or more phasing errors resulting from asynchronous incorporation of the one or more nucleotide species during the sequencing reaction;
using a simulation model to generate predicted sequence data, wherein the simulation model simulates possible state transitions for molecules present at a K-th base during an N-th nucleotide flow of the sequencing reaction, wherein K and N denote indices associated with bases and the nucleotide flows from the sequencing reaction, and wherein the simulation model uses one or more parameters chosen from:
an estimated reactivated molecules rate (RMR),
an estimated termination failure rate (TFR), and
an estimated inactivated molecules rate (IMR);
comparing the raw sequencing data with the predicted sequence data; and
based on the comparing, outputting a candidate sequence for the sample nucleic acid.

2. The method of claim 1, further comprising optimizing a solver function based on the comparing of the raw sequencing data with the predicted sequencing data, wherein the outputting of the candidate sequence is based on the optimizing.

3. The method of claim 1, wherein the simulation model comprises simulating possible state transitions for situations where the K-th base matches the N-th nucleotide flow by modeling (i) a proportion of molecules that will remain active or become active and not incorporate base K in nucleotide flow N using a first set of state transition factors and (ii) a proportion of molecules that will remain active and incorporate base K in the nucleotide flow N using a second set of state transition factors.

4. The method of claim 3, wherein:
the first set of state transition factors comprises a state transition factor [1–TFR], and a state transition factor [TFR], a state transition factor [RMR]; and
the second set of state transition factors comprises a state transition factor [TFR], and a state transition factor [RMR].

5. The method of claim 1, wherein the simulation model comprises simulating possible state transitions for situations where the K-th base does not match the N-th nucleotide flow by modeling (i) a proportion of molecules that will remain active or become active and not incorporate base K in nucleotide flow N using a first set of state transition factors and (ii) a proportion of molecules that will remain active and incorporate base K in the nucleotide flow N using a second set of state transition factors.

6. The method of claim 5, wherein:
the first set of state transition factors comprises a state transition factor [1–TFR], a state transition factor [TFR], and a state transition factor [RMR], and
the second set of state transition factors comprises a state transition factor [TFR], a state transition factor [RMR], and a state transition factor,
wherein M is a number such that the (N–M)-th nucleotide flow matches the K-th base.

7. The method of claim 1, wherein the sequencing reaction utilizes a reversible terminator to reversibly terminate primer extension along the sample nucleic acid.

8. The method of claim 7, wherein the reversible terminator comprises a 3-prime O-blocked reversible terminator having a blocking group linked to an oxygen atom of a 3-prime hydroxyl group of a pentose of the reversible terminator.

9. A nucleic acid sequencing system, comprising:
a sequencing instrument configured to receive a sample nucleic acid, at least one nucleotide, a primer, and a polymerase, and to subject the sample nucleic acid to a sequencing reaction comprising a total number of nucleotide flows of greater than 160 to produce raw sequencing data, wherein the raw sequencing data is generated from detecting signal emission in response to incorporation of nucleotide species during the sequencing reaction, the raw sequencing data comprising one or more phasing errors resulting from asynchronous incorporation of the one or more nucleotide species during the sequencing reaction; and
a processor configured to:
receive the raw sequencing data,
use a simulation model to generate predicted sequence data, wherein the simulation model determines:
possible state transitions for molecules present at a K-th base during an N-th nucleotide flow of the sequencing reaction, wherein K and N denote indices associated with bases and the nucleotide flows from the sequencing reaction, and wherein the simulation model uses one or more parameters chosen from:
an estimated reactivated molecules rate (RMR),
an estimated termination failure rate (TFR), and
an estimated inactivated molecules rate (IMR);

compare the raw sequencing data with the predicted sequence data; and
based on the comparison, output a candidate sequence for the sample nucleic acid.

10. The system of claim 9, wherein the processor is further configured to optimize a solver function based on the comparison of the raw sequencing data with the predicted sequencing data, wherein the candidate sequence is output based on the optimization.

11. The system of claim 9, further comprising a flow controller configured to control timing and quantity of the nucleotide flows, the primer, and the polymerase to the sequencing instrument.

12. The system of claim 11, wherein the at least one nucleotide comprises 2" dideoxynucleotides in a form of ddATP, ddCTP, ddGTP, and ddTTP, and the flow controller is configured to:
flow a mixture of ddATP, ddCTP, ddGTP, and ddTTP concurrently into the sequencing instrument, or
flow each of ddATP, ddCTP, ddGTP, and ddTTP, one at a time, into the sequencing instrument, or
both.

13. The system of claim 9, wherein the sequencing instrument comprises a semiconductor sensing device configured to detect electrical signal emission.

14. An apparatus, comprising:
a machine-readable memory; and
a processor configured to execute machine-readable instructions, the instructions which when executed cause the apparatus to:
generate raw sequencing data obtained from detecting signal emission resulting from incorporation of nucleotide species during a sequencing reaction comprising a total number of nucleotide flows of greater than 160 for sequencing a sample nucleic acid, the raw sequencing data comprising one or more phasing errors resulting from asynchronous incorporation of the one or more nucleotide species during the sequencing reaction;
use a simulation model to generate predicted sequence data, wherein the simulation model determines:
possible state transitions for molecules present at a K-th base during an N-th nucleotide flow of the sequencing reaction, wherein K and N denote indices associated with bases and the nucleotide flows from the sequencing reaction, and wherein the simulation model uses one or more parameters chosen from:
an estimated reactivated molecules rate (RMR),
an estimated termination failure rate (TFR), and
an estimated inactivated molecules rate (IMR);
compare the raw sequencing data with the predicted sequence data; and
based on the comparison, output a candidate sequence for the sample nucleic acid.

15. The apparatus of claim 14, wherein the instructions when executed further cause the apparatus to optimize a solver function based on the comparison of the raw sequencing data with the predicted sequencing data, and wherein the candidate sequence is output based on the optimization.

* * * * *